United States Patent
Rodgers et al.

(10) Patent No.: US 11,268,107 B2
(45) Date of Patent: Mar. 8, 2022

(54) SMAD7 GENE DELIVERY INTO MUSCLE CELLS

(71) Applicants: Washington State University, Pullman, WA (US); Baker Heart and Diabetes Institute, Melbourne (AU)

(72) Inventors: Buel Dantese Rodgers, Pullman, WA (US); Paul Gregorevic, Melbourne (AU)

(73) Assignees: Washington State University, Pullman, WA (US); Baker Heart and Diabetes Institute, Melbourne (AU)

( * ) Notice: Subject to any disclaimer, the term of this patent is extended or adjusted under 35 U.S.C. 154(b) by 524 days.

(21) Appl. No.: 15/568,244

(22) PCT Filed: Apr. 22, 2016

(86) PCT No.: PCT/US2016/029018
§ 371 (c)(1),
(2) Date: Oct. 20, 2017

(87) PCT Pub. No.: WO2016/172608
PCT Pub. Date: Oct. 27, 2016

(65) Prior Publication Data
US 2018/0112232 A1    Apr. 26, 2018

Related U.S. Application Data

(60) Provisional application No. 62/151,547, filed on Apr. 23, 2015.

(51) Int. Cl.
*C12N 15/86* (2006.01)
*A61P 21/00* (2006.01)

(52) U.S. Cl.
CPC .............. *C12N 15/86* (2013.01); *A61P 21/00* (2018.01); *C12N 2750/14143* (2013.01); *C12N 2750/14171* (2013.01)

(58) Field of Classification Search
None
See application file for complete search history.

(56) References Cited

U.S. PATENT DOCUMENTS

| 2013/0136729 A1 | 5/2013 | French et al. |
| 2013/0267456 A1 | 10/2013 | Wang et al. |
| 2014/0128349 A1 | 5/2014 | Marks et al. |

FOREIGN PATENT DOCUMENTS

| WO | WO 2004/058988 | 7/2004 |
| WO | WO 2005/049850 | 6/2005 |
| WO | WO 2014/167253 | 10/2014 |

OTHER PUBLICATIONS

Kollias et al, (Mol and Cellular Biology, 26(16): 6248-6260, 2006), (Year: 2006).*
Davey et al., "Integrated Expression Analysis of Muscle Hypertrophy Identifies Asb2 as a Negative Regulator of Muscle Mass," *JCI Insight*, vol. 1:e85477, 2016.
Elkina et al., "The Role of Myostatin in Muscle Wasting: An Overview," *J. Cachexia Sacropenia Muscle*, vol. 2:143-151, 2011.
Gregorevic, et al., "Systemic Delivery of Gene to Striated Muscles using Adeno-Associated Viral Vectors," *Nat. Med.*, vol. 10:828-834, 2004.
Hagg et al., "Using AAV Vectors Expressing the β2-adrenoceptor or Associated Gα Proteins to Modulate Skeletal Muscle Mass and Muscle Fibre Size," *Sci. Rep.*, vol. 6:23042, 2016.
Kollias et al., "Smad7 Promotes and Enhances Skeletal Muscle Differentiation," *Mol. Cell. Biol.*, vol. 26:6248-6260, 2006.
Lee et al., "Treating Cancer Cachexia to Treat Cancer," *Skeletal Muscle*, vol. 1:1-5, 2011.
Anonymous, "Vector: pAAV-MCS," Feb. 27, 2015, XP055493842, retrieved from the internet: URL:https://web.archive.org/web/20150227170458/https://plasmid.med.harvard.edu/PLASMID/GetVectorDetail.do?vectorid=221, retrieved on Jul. 19, 2018 (2 pages).
Extended European Search Report dated Sep. 7, 2018, for European Application No. 16784014.9 (11 pages).
Huang et al., "Construction and expression of adeno-associated virus vectors of Smad 6 and Smad 7 genes in human renal tubule epithelial cells," *Chin J Cell Mol Immunol* 20(3):274-277, 2004 (and accompanying English-language abstract).
Kelly and Russell, "MicroRNAs and the Regulation of Vector Tropism," *Mol Ther* 17(3):409-416, Dec. 23, 2008.
Keppler et al., "AAV Mediated Gene Transfer of Smad7 in Different Models of Cystic Kidney Disease," *Mol Ther* 13(Suppl 1):S85 (Abstract 220), 2006.

* cited by examiner

Primary Examiner — Anoop K Singh
Assistant Examiner — Magdalene K Sgagias
(74) Attorney, Agent, or Firm — Klarquist Sparkman, LLP

(57) ABSTRACT

Described herein are vectors, such as adeno-associated virus (AAV) vectors, and recombinant AAV expressing Smad7. The disclosed AAV vectors and rAAV can be used for therapeutic applications in the treatment and amelioration of muscle wasting, cardiac and/or skeletal muscle wasting associated with cancer cachexia.

8 Claims, 29 Drawing Sheets

Specification includes a Sequence Listing.

lung heart kidney spleen

TA muscle

Con     Smad7

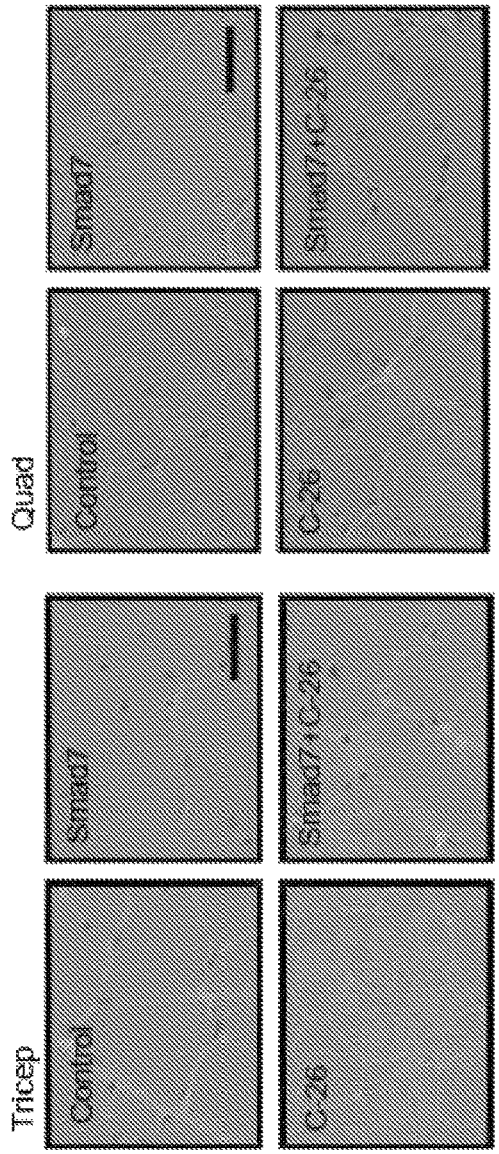
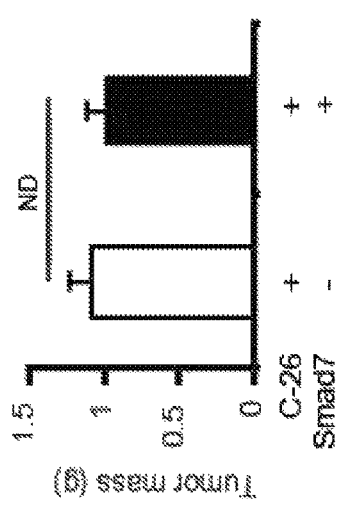
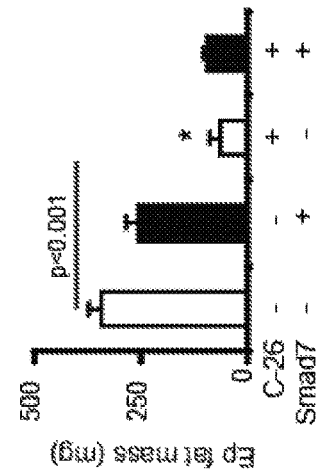
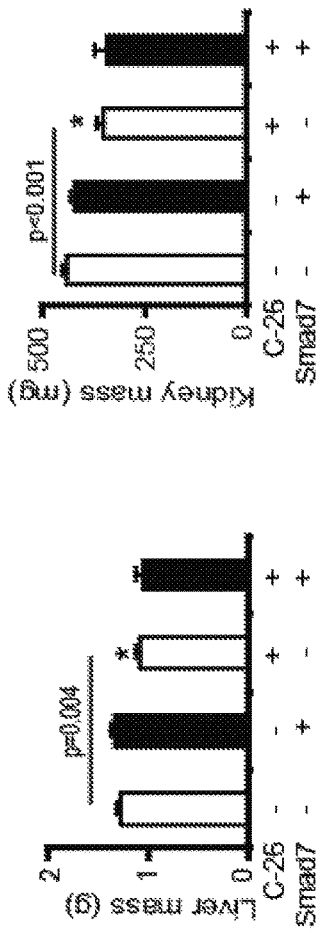
FIG. 8D
FIG. 8E
FIG. 8F
FIG. 8G

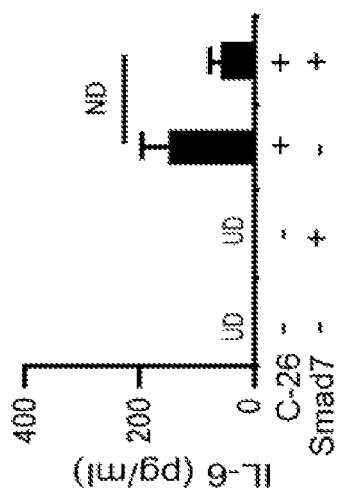
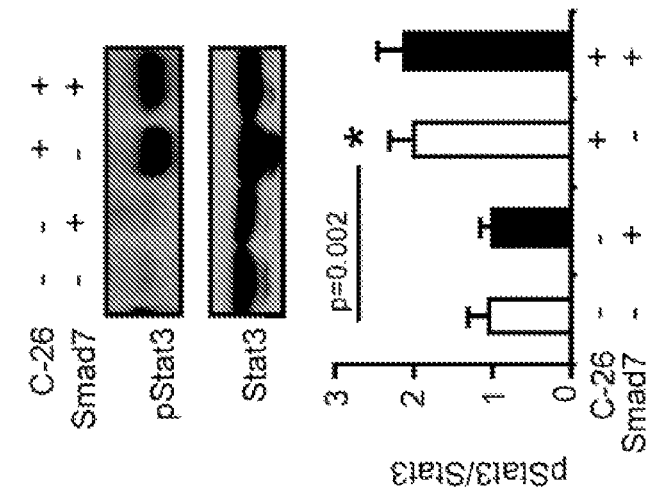
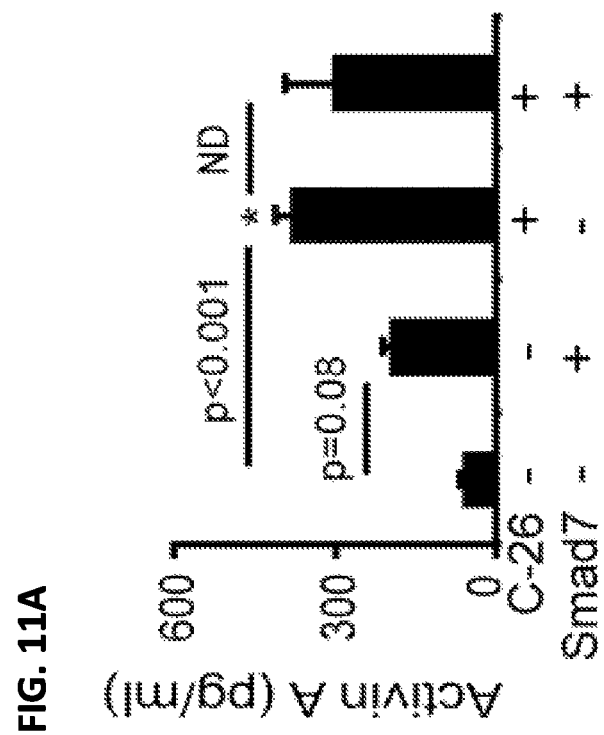
FIG. 11A
FIG. 11B
FIG. 11C

Restriction Sites

| | | | | | |
|---|---|---|---|---|---|
| PstI (6) | SspI (1083) | AccI (1989) | XmaI (2700) | BglII (2757) | SspI (3934) |
| PvuII (11) | ClaI (1320) | PstI (2061) | SmaI (2702) | SspI (2893) | ApaLI (3956) |
| XmaI (40) | EcoRI (1326) | SacII (2090) | BamHI (2705) | SphI (3081) | SspI (4320) |
| SmaI (42) | PvuII (1713) | EcoRV (2247) | XbaI (2711) | NotI (3274) | ApaLI (4453) |
| XmaI (51) | SacII (1746) | PvuII (2316) | SalI (2717) | XmaI (3366) | DraI (4547) |
| SmaI (53) | PstI (1795) | PvuII (2358) | AccI (2718) | SmaI (3368) | FspI (4902) |
| NotI (143) | XmaI (1803) | ApaLI (2461) | PstI (2727) | XmaI (3377) | DraI (5239) |
| SacI (727) | ApaI (1804) | PstI (2525) | HindIII (2729) | SmaI (3379) | DraI (5258) |
| SacII (814) | SmaI (1805) | PvuII (2633) | XhoI (2737) | PvuII (3410) | ApaLI (5699) |
| SspI (1067) | SalI (1988) | EcoRI (2694) | XhoI (2751) | PstI (3419) | |

SMAD7 GENE DELIVERY INTO MUSCLE CELLS

CROSS REFERENCE TO RELATED APPLICATIONS

This is the U.S. National Stage of International Application No. PCT/2016/029018, filed Apr. 22, 2016, published in English under PCT Article 21(2), which claims priority to U.S. Provisional Application No. 62/151,547, filed on Apr. 23, 2015, which is herein incorporated by reference in its entirety.

ACKNOWLEDGEMENT OF FEDERAL FUNDING

This invention was made with government support under grant number IOS1147275 awarded by the National Science Foundation. The government has certain rights in the invention.

INCORPORATION BY REFERENCE OF SEQUENCE LISTING

The Sequence Listing is submitted as an ASCII text file named 96554-09_ST25.txt, created on Oct. 20, 2017, 8.97 KB, which is incorporated by reference herein.

BACKGROUND

Tumor-derived factors induce cachexia, a state of pronounced weight loss, frailty and fatigue characterized by severe atrophy of muscle and fat, in up to 80% of patients with advanced cancers (Tisdale, *Physiol Rev* 89, 381-410, 2009; Fearon et al., *Cell Metabolism* 16, 153-166, 2012). Much interest has centered on the therapeutic prospects of inhibiting Type IIB activin receptor (ActRIIB) ligands in these patients, as this pathway stimulates muscle catabolism and expression of these ligands is often elevated with muscle wasting (Fearon et al., *Cell Metabolism* 16, 153-166, 2012; Lee & Glass, *Skelet Muscle* 1, 2, 2011, doi: 10.1186/2044-5040-1-2). In fact, circulating forms of a modified ActRIIB or other "ligand traps" (e.g., soluble ActRIIB, ACE-031, immunoneutralization, etc.) can reverse muscle wasting and increase lifespan (Klimek et al., *Biochem Biophys Res Commun* 391, 1548-1554, 2010; Zhou et al., *Cell* 142, 531-543, 2010) despite the fact that other pro-cachectic cytokines remain elevated. Thus, interventions that selectively prevent ActRIIB signaling in muscle could prove instrumental in treating cancer cachexia (Zhou et al., *Cell* 142, 531-543, 2010). Targeting ActRIIB ligands in circulating or extracellular environments, however, can produce adverse and serious off-target effects as these ligands are critical to many organ systems including reproduction and angiogenesis (Massague, *Nat Rev Mol Cell Biol* 13, 616-630, 2012).

For instance, a clinical study of ACE-031, a peptibody ligand trap largely composed of the extracellular domain of ActRIIB, was terminated prematurely (Smith & Lin, *Curr Opin Support Palliat Care* 7, 352-360, 2013) due to the induction of signs often seen in patients with heredity hemorrhagic telangiectasia (HHT), which included bleeding from mucous membranes and skin vasodilation. Thus, other approaches that target ActRIIB ligands in circulation could produce similar off-target effects. This disease results from mutations in two signaling proteins, endoglin or activin like kinase-1, that ultimately impair TGFβ receptor signaling in endothelial cells. Blood vessel integrity is similarly compromised in patients with HHT and in mouse models of the disease (Bourdeau et al., *J Clin Invest* 104, 1343-1351, 1999; Bourdeau et al., *Am J Pathol* 156, 911-923, 2000; Bourdeau, et al., *Trends Cardiovasc Med* 10, 279-285, 2000; Bourdeau et al., *Am J Pathol* 158, 2011-2020, 2001; Satomi, et al., *Stroke* 34, 783-789, 2003; Torsney et al., *Circulation* 107, 1653-1657, 2003). In fact, these models develop hemorrhaging in the nose, ears and tail, all of which are readily visible with external examination and can even cause partial tail loss. Hemorrhaging also occurs in several internal organs and is most apparent histologically in the liver and lungs, although focal sites of hemorrhaging were again clearly evident with gross examination. Some mice even suffered strokes from arteriovenous malformations in the brain and this presented as muscle flaccidity and ptosis, which again was readily detected.

Once activated, ActRIIB recruits Type I activin receptors (activin like kinase (ALK)4/5) to form an activated ActRIIB:ALK4/5 complex that phosphorylates Smad2/3 (Massague, *Nat Rev Mol Cell Biol* 13, 616-630, 2012). These receptor Smads then bind Smad4, allowing the complex to enter the nucleus and modify a protein degradation transcriptional program that up-regulates the E3 ubiquitin ligases, MuRF1 and MAFbx, and dephosphorylates Akt (Amirouche et al., *Endocrinology* 150, 286-294, 2009; Trendelenburg et al., *Am J Physiol Cell Physiol* 296, C1258-1270, 2009). This pathway also upregulates Smad7 expression, as a form of intracellular negative feedback, which prevents Smad2/3 phosphorylation and promotes ActRI degradation (Chen et al., *Genes Dev* 12, 2144-2152, 1998).

SUMMARY OF EXEMPLARY ASPECTS

We sought to develop an improved strategy for treating cachexia by attenuating the intracellular ActRIIB signaling pathway, rather than the ligands (myostatin, activin & GDF-11), as this could potentially avoid the off-target effects of ligand traps. We have shown that increasing Smad7 expression specifically in striated muscle could ameliorate muscle wasting by attenuating ActRIIB signaling. To achieve this goal while avoiding the potential off-target effects of ligand traps, we utilized a recombinant adeno-associated viral vector (serotype 6, rAAV6) with specific tropism for striated muscle (Gregorevic et al., *Nat Med* 10, 828-834, 2004; incorporated herein by reference). In fact, our studies indicate that the overexpression of Smad7 specifically in striated muscle not only enhances muscle mass and function, but can prevent wasting under different conditions of muscle wasting including but not limited to cancer cachexia, diabetes, obesity, cardiovascular diseases and aging.

Particular aspects demonstrate that patients with advanced cancer often succumb to severe wasting of striated muscle. Activation of ActRIIB is considered a key mechanism underlying this catabolism, although interventions to prevent it by antagonizing circulating ActRIIB ligands have been hampered by off-target effects. Attenuating ActRIIB signaling by overexpressing Smad7 with recombinant adeno-associated viral vectors (serotype 6, rAAV6) [rAAV:Smad7] that have defined tropism for striated muscle enhanced skeletal muscle mass and function in healthy mice, while in mice bearing C-26 tumors it prevented wasting of skeletal and cardiac muscle independent of tumor burden and serum levels of pro-cachectic ligands.

According to further aspects, rAAV:Smad7 also prevented wasting in inhibin-a knockout mice and with the overexpression of myostatin or activin A. No off-target effects were detected as Smad7 expression was limited to only striated muscle, as were biomarkers for Smad7 activity. Mechanistically, Smad7 abolished Smad2/3 signaling and inhibited expression of the atrophy-related ubiquitin ligases MuRF1 and MAFbx.

According to yet further aspects, these findings indicate that vector-mediated muscle-specific expression of Smad7 is not only a novel approach for preventing muscle wasting or even excessive ActRIIB signaling, but also a means to enhance muscle mass and function with limited risks of serious off-target effects.

Thus, there is provided herein a composition comprising a Smad7 gene or cDNA in a recombinant adeno-assisted virus (rAAV) construct, wherein the rAAV construct provides expression (constititively or otherwise) of the Smad7 gene or cDNA in muscle cells. By way of non-limiting examples of such compositions, in certain embodiments the rAAV construct is serotype 6 (rAAV6), serotype 8 (rAAV8), or serotype 9 (rAAV9). By way of non-limiting examples of such compositions, in certain embodiments the Smad7 gene or cDNA is of human, mouse, equine, bovine, ovine, canine, or porcine origin.

In additional embodiments, the rAAV construct comprises a tissue-specific promoter or enhancer that directs expression of the Smad7 gene or cDNA in muscle cells. Alternatively, the rAAV construct provides expression of the Smad7 gene or cDNA in cardiac muscle cells, skeletal muscle cells, or both. And in yet additional embodiments, the rAAV construct comprises a tissue-specific silencer that limits expression of the Smad7 gene or cDNA to muscle cells or to heart cells.

An additional embodiment is a method of enhancing muscle mass and/or strength in a subject, comprising administering to the subject a therapeutically effective amount of a comprising a Smad7 gene or cDNA in a recombinant adeno-assisted virus (rAAV) construct as provided herein. In examples of such methods, the subject is not diagnosed with a muscle-wasting disorder or disease. For instance, the subject in such method may be generally healthy. Thus, contemplated herein are cosmetic or elective uses of the compositions and methods described herein, to enhance above baseline or "normal" the muscle mass and/or strength of a subject.

Another embodiment is a method of treating muscle wasting (for instance, wasting of cardiac muscle, skeletal muscle, or both) in a subject diagnosed with a cancer cachexia, comprising selecting a subject with cancer cachexia and administering to the subject a therapeutically effective amount of the composition of any one of the compositions comprising a Smad7 gene or cDNA in a recombinant adeno-assisted virus (rAAV) construct, wherein the rAAV construct provides expression (constititively or otherwise) of the Smad7 gene or cDNA in muscle cells. Also provided are methods of treating muscle wasting to increase muscle strength and/or muscle volume using such a composition. A further embodiment is a method of inhibiting or preventing muscle wasting in a subject, comprising administering to the subject a therapeutically effective amount of such a composition.

By way of example in treatment method embodiments, the muscle wasting in some instances is caused by a chronic disorder. Without limitation, in various instances the chronic disorder comprises cancer, aging (sarcopenia), muscular dystrophy, myopathies, kidney disease, chronic obstructive pulmonary disorder, chronic infection, AIDS, disuse atrophy, neuromuscular injury, neuropathies, obesity, cardiovascular disease, or a combination of two or more thereof. Alternatively, the muscle wasting is caused by microgravity stress.

In any of the provided method embodiments, the composition will in some instances be delivered via intramuscular or intravenous injections.

In any of the provided method embodiments, administering the rAAV will in some cases involve administration of a single dose of rAAV. In other cases, the methods will involve administration of multiple doses of rAAV.

The foregoing and other features and advantages will become more apparent from the following detailed description of several embodiments, which proceeds with reference to the accompanying figures.

BRIEF DESCRIPTION OF THE DRAWINGS

(FIG. 1A-1B) Injection of mouse limb muscles with rAAV6:Smad7 increased muscle mass between 7 and 28 days. (FIG. 1C-1D) Muscle hypertrophy was associated with increased myofiber diameter (*, p=0.03 vs. control, ~500 myofibers counted in three muscles per treatment, t-test). Scale bar, 100 μm. (FIG. 1E-1F) Mice were injected IV with rAAV6:Smad7 and after 28 days, this resulted in hypertrophy of the TA (*, p=0.02 vs. control, n=3, t-test), quadriceps (*, p=0.004 vs. control, n=3, t-test) and triceps muscles (*, p=0.003 vs. control, n=3, t-test) and elevated Smad7 protein expression in TA, quadriceps and heart. (FIG. 1G) rAAV6:Smad7 suppressed phosphorylation of Smad3 at all three time points (*, p=0.006 vs. control, n=4, T-test) post-administration (FIG. 1H) Mice injected with either rAAV6:Smad3-CA (n=3), rAAV6:Smad7 (n=5), or rAAV6:Smad7 and rAAV6:Smad3-CA (n=5) were examined 28 days post-treatment for effects on TA mass and protein expression (*, p<0.001 vs. control, #, p<0.001 vs. control, +, p<0.001 vs. Smad7, by one-way ANOVA). (FIG. 1I) Hematoxylin and eosin-stained cryosections demonstrate smaller muscle fibers in muscles examined 28 days after receiving rAAV6:Smad7 and rAAV6:Smad3-CA compared with rAAV6:Smad7 alone. Scale bar, 100 μm.

(FIG. 2A) Smad7 protein expression (as determined by Western blotting) was detected in skeletal muscles and the heart, but not in liver, kidney, lung, spleen or fat of mice following intravenous administration of rAAV6:Smad7. (FIG. 2B) Gene expression of Smad2/3 gene targets in non-muscle tissues of wild-type mice (sham), those with C26 tumors and C26 mice injected with rAAV6:Smad7 (CTGF, connective tissue growth factor; COL1A1, collagen type 1a1; PAI1, plasminogen activator inhibitor 1; FN, fibronectin). No significant differences between C26 and C26+Smad7 were detected (*p<0.05 compared to sham). (FIG. 2C) Histological evidence, using Van Gieson stain, of intact blood vessels and the lack of haemorrhaging in tissues from mice given rAAV6:Smad7. (FIG. 2D) Myofiber diameter was increased by rAAV6:Smad7 as demonstrated by representative hematoxylin and eosin stained cryosections (scale bar, 100 μm).

(FIG. 3A) Muscles examined 14 days after intramuscular rAAV6:Smad7 injection demonstrated up-regulated fractional rates of protein synthesis (n=5-6, t-test). (FIG. 3B) Mice were injected with rAAV6:

Smad7 and after 28 days, there was no increase in phosphorylation of Akt$^{S473}$ or its substrates GSK3β$^{S9/21}$ and TSC2$^{S939}$ (ND=not different, n=6-7, t-test). rAAV6:Smad7 increases phosphorylation of S6RP$^{S235/236}$ (n=6 per treatment, t-test) and 4EBP1$^{T37/42}$ (n=4-5 per treatment, t-test). (FIG. 3C) Akt kinase activity was not altered 28 days after rAAV6:Smad7 delivery. Neg=negative control with no ATP added. pAkt was normalized to total Akt levels (n=5, t-test). (FIG. 3D) Rapamycin administration inhibited phosphorylation of S6RP$^{S235/236}$ (n=4-5, two-way ANOVA) and 4EBP1$^{T37/43}$ (n=3, two-way ANOVA). (FIG. 3E) Rapamycin was administered daily to animals treated with rAAV6:Smad7 (n=6). Tibialis anterior (TA) mass expressed as a percentage change to the contralateral control muscle. (FIG. 3F) rAAV6:Smad7 suppressed transcription of MAFbx (n=9-11, t-test) and MuRF1 (n=9-11, t-test) while rAAV6:Smad3-CA increased both (n=4, t-test) 14 days after treatment. (FIG. 3G) Co-administration of rAAV6:Smad3-CA with rAAV6:Smad7 prevented the inhibitory effect of Smad7 on MAFbx (n=5) and MuRF1 (n=5) transcription (n=5, t-test).

(FIG. 4A-4B) Muscle mass and myofiber fiber was examined in wild-type and myostatin-null mice 14 days (*, p<0.001 vs. Mstn+/+ control, #, p=0.003 vs. Mstn−/− control, +, p<0.001 vs. Mstn−/− control, n=5-6, two-way repeated measures ANOVA) and 28 days (*, p<0.001 vs. Mstn+/+ control, #, p=0.001 vs. Mstn−/− control, +, p=0.01 Mstn−/− vs. Mstn+/+, n=6-8, two-way repeated measures ANOVA) after local rAAV6:Smad7 administration. Scale bar=100 μm. (FIG. 4C) Smad7 induced comparatively less hypertrophy in myostatin null mice after 28 days (*, p=0.03 vs. control, two-way ANOVA). (FIG. 4D) Inhibition of Smad3$^{S432/435}$ phosphorylation by Smad7 was conserved in myostatin-null mice (*, p=0.006 vs. control, n=4, two-way repeated measures ANOVA) compared with wild-type mice (*, p=0.001 vs. control, n=4, two-way repeated measures ANOVA). (FIG. 4E-4F) rAAV6:Smad7 administered alone or with rAAV6:myostatin (*, p<0.001 vs. control, #, p<0.001 vs. control, +, p=0.004 vs. Smad7, n=7-15, one-way ANOVA) or rAAV6:Activin A (*, p<0.001 vs. control, #, p=0.003 vs. control, n=3-6, one-way ANOVA) 28 days after treatment. (FIG. 4G) Smad3$^{S432/435}$ phosphorylation in muscles expressing Myostatin (*, p=0.015 vs. control, #, p<0.001 vs. control, +, p<0.001 vs. Mstn treatment, n=4-9, one-way ANOVA) or Activin A (*, p=0.01 vs. control, #, p<0.001 vs. control, treatment, +, p<0.001 vs. Act A treatment n=5-7, one-way ANOVA) alone and in the presence of Smad7.

(FIG. 5A) Activin A and (FIG. 5B) myostatin transgene gene expression were determined by RT-PCR 28 days after rAAV6 administration. Activin A or myostatin gene expression did not differ when co-expressed with Smad7 as compared with the expression level of activin A or myostatin alone (ND=not different, n=3-6, t-test). (FIG. 5C) Myostatin protein levels in tibialis anterior muscle of mice similarly given rAAV6:Smad7 and/or rAAV6:Mstn. Activin A protein levels were also measured in mice given rAAV6:ActA, but were not detected as ActA is secreted and not stored intra- or extracellularly.

(FIG. 6A) Implantation of C-26 tumors ~21 days prior to examination induced a 25% decrease in body mass (*, p<0.001 vs. control, tumor-free mass, n=13-14, t-test). (FIG. 6B-6C) Quadriceps and heart mass were decreased in C-26 tumor bearing mice (*, p<0.001 vs. control, n=13-14, t-test) (FIG. 6D) Epididymal fat mass was decreased in mice bearing C-26 tumors (*, p<0.001 vs. control, n=6-7, t-test). (FIG. 6E) Increased Smad7 expression prevented loss of peak tetanic force (*, p<0.001 vs. control, #, p=0.03 vs. control, n=8-9, two-way ANOVA) produced by TA muscles in situ from C-26 tumor-bearing mice. (FIG. 6F) Cross-sections of TA muscle were double labeled with laminin (red) and MHCIIa (type IIa, green) to assess the area of type IIa and type IIx/b fibers (non-reacting) (FIG. 6G) Smad7 prevented reductions in the area of type IIa (*, p<0.001 vs. control, #, p<0.001 vs. control, +, p<0.001 vs. C-26, n=8, two-way ANOVA) and type IIx/b (*, p=0.002 vs. control, +, p=0.001 vs. C-26, n=8, two-way ANOVA) fibers in the muscles of tumor-bearing mice. (FIG. 6H-6I) Fiber type proportions the muscles of healthy mice and tumor bearing mice receiving rAAV6:Smad7 or sham vector (*, p=0.02 vs. control group, n=8, two-way ANOVA).

(FIG. 7A) rAAV6:Smad7 delivered to limb muscles of mice receiving C-26 tumors preserved mass (*, #, p<0.001 vs. control, +, p<0.001 vs. C-26, n=11-14), (FIG. 7B) force producing capacity (*, #, p<0.001 vs. control, +, p<0.001 vs. C-26, n=11-14), and (FIG. 7C) myofiber cross-sectional area (CSA, *, #, p<0.001 vs. control, +, p<0.001 vs. C-26, n=8). (FIG. 7D Smad7 expression in muscles from healthy and tumor-bearing mice (western blot). (FIG. 7E) rAAV6:Smad7 delivered 7 days (*, p<0.001 vs. control, #, p=0.01 vs. control, +, p<0.001 vs. C-26 control, n=5-7) and 14 days (*, p=0.03 vs. control, #, p=0.004 vs. control, +, p=0.02 vs. C-26 control, n=5-6) after tumor implantation (when tumor burden was increased, right panel) preserved muscle mass (*, p<0.001 vs. 7 days, n=10, t-test). (FIG. 7F) Systemic rAAV6:Smad7 treatment reduced loss of body mass (*, p=0.005 vs. control, #, p<0.001 vs. control), and (FIG. 7G) prevented loss of muscle mass (Gastrocnemius—Ga, *, p<0.001 vs. control, #, p<0.001 vs. control, +, p=0.04 vs. C-26, n=4-7. Quadriceps—Qd, *, p<0.001 vs. control, #, p<0.001 vs. control, +, p=0.01 vs. control, n=4-14. Triceps—Tr, *, p<0.001 vs. control, #, p=0.002 vs. control, +, p=0.007 vs. C-26, n=4-14.). (FIG. 7H) Images of control and tumor-bearing mice receiving sham or rAAV6:Smad7. (FIG. 7I) Hematoxylin & eosin-stained cryosections of TA muscles from control and tumor-bearing mice receiving sham or rAAV6:Smad7. (FIG. 7J) TA muscle mass (*, p<0.001 vs. groups, n=4) and (FIG. 7K) myofiber diameter (*, p=0.02 vs. control, #, p=0.004 vs. control, +, p=0.006 vs. inha-KO) in inhibin-null mice (inha-KO) 4 weeks after injection of rAAV6:Smad7. Data analyzed by two-way ANOVA unless indicated. Scale-bars, 100 μm.

FIGS. 8A-8K show, according to particular aspects, systemic rAAV6:Smad7 administration does not affect visceral organ mass or fat mass. (FIG. 8A-8B) Smad7 protein and gene expression were examined in heart (*, p=0.001 vs. control, n=3, one-way ANOVA), quadriceps (*, p=0.02 vs. control, n=3, one-way ANOVA) and TA muscle (+, p=0.008 vs. control, n=3, one-way ANOVA) from healthy and tumor-bearing mice. (FIG. 8C) TA muscle mass was preserved by systemic rAAV6:Smad7 administration (*, p<0.001 vs. control, #, p<0.001 vs. control, +, p<0.001 vs. C-26, n=8-14, two-way ANOVA). (FIG. 8D) Representative images demonstrate that rAAV6:Smad7 preserves triceps and quadriceps muscle mass. (FIG. 8E) Tumor masses were not different between C-26 tumor bearing mice receiving sham vector or rAAV6:Smad7 (ND=not different between groups, n=8-14, t-test). (FIG. 8F-8G) Systemic rAAV6:Smad7 administration did not prevent tumor-induced loss of liver (*, p=0.004 vs. control, n=8-14, two-way ANOVA), kidney (*, p<0.001 vs. control, n=4-7, two-way ANOVA) or epididymal fat mass (*, p<0.001 vs. control, n=3-7, two-way ANOVA). (FIG. 8H-8U) Systemic rAAV6:Smad7 administration prevented cardiac atrophy (mass normalized relative to tibial bone length) in tumor bearing mice (*, p<0.001 vs. control, #, p<0.001 vs. control, +, p<0.001 vs. C-26, n=7-11, two-way ANOVA). Hematoxylin & eosin scale bar, 100 μm. Photograph scale, 0.2 cm. (FIG. 8J) Atrial weight was normalized over tibial bone length. (FIG. 8K) Smad7 did not affect atrial weight or lung mass (normalized to tibial bone length, ND=not different, n=4-11, two-way ANOVA).

(FIG. 9A) Fat mass (*, p=0.001 vs. 11 week old WT control, +, p<0.001 vs. 12 week old WT control), lean mass (*, p=0.04 vs. 9 week old WT control, +, p=0.005 vs. 10 week old WT control, #, p<0.001 vs. 11-12 week old WT controls) and total body mass (*, p=0.008 vs. 10 week old WT control, +, p<0.001 vs. 11-12 week old WT controls) was assessed in inhibin-α null mice and their littermate controls from 6 weeks of age (n=4, Data analyzed by two-way ANOVA). (FIG. 9B) Gonadal tumor mass was increased in inhibin-α null mice compared with wild type litter mates (*, p=0.008 vs. WT controls, t-test, n=4). (FIG. 9C) Quadriceps mass of inhibin-α null mice was decreased compared to WT controls (*, p=0.001 vs. WT controls, t-test, n=4).

(FIG. 10A) Serum levels of activin A and activin B were measured in cachectic mice (UD=undetermined, *, p<0.001 vs. control, n=4-11, t-test). (FIG. 10B) Serum was collected 21 days after implanting tumors and injecting rAAV6:Smad7 and used in activated Smad2/3 reporter assays with C2C12 cells (*, p=0.01 vs. control, n=3, repeated three times, two-way ANOVA, ND=not different). (FIG. 10C Smad3$^{S432/435}$ phosphorylation was measured in TA muscles from C-26 tumor bearing mice (*, p=0.01 vs. control, #, p=0.005 vs. control, +, p<0.001 vs. C-26, n=8-13, two-way ANOVA) and inhibin-α null mice (*, p=0.03 vs. control, #, p<0.001 vs. control, +, p<0.001 vs. inhibin-α null, n=4, two-way ANOVA) treated with rAAV6:Smad7. (FIG. 10D) Total Foxo protein levels were determined by Western blotting Foxo1 (*, p<0.001 vs. control, #, p=0.04 vs. C-26, n=5-6 per treatment, two-way repeated measures ANOVA) and Foxo3 (*, p<0.001 vs. control, #, p=0.04 vs. C-26, n=5-6 per treatment, two-way repeated measures ANOVA) in healthy mice and tumor-bearing mice. (FIG. 10E-10F) Smad7 suppressed transcription of Foxo1 (*, p<0.001 vs. control, #, p<0.001 vs. C-26, n=5-8, two-way ANOVA) and Foxo3 (*, p=0.002 vs. control, #, p=0.004 vs. C-26, n=5, two-way ANOVA), as well as MuRF1 (*, p<0.001 vs. control, #, p<0.01 vs. C-26, n=4-8, two-way ANOVA) and MAFbx (*, p<0.001 vs. control, #, p<0.001 vs. C-26, n=4-8, two-way ANOVA).

FIGS. 11A-11E show, according to particular aspects, Smad7 does not alter Foxo phosphorylation or NF-κB signaling in cachexia. (FIG. 11A) Serum Activin A levels were measured via ELISA 21 days after implanting tumors and injecting rAAV6:Smad7 or sham vector (*, p<0.001 vs. control, n=4 per cohort, two-way ANOVA). (FIG. 11B) Serum IL-6 levels in tumor-bearing mice treated with rAAV6:Smad7 or sham vector were measured via ELISA (n=4-5). (FIG. 11C) Stat3, (FIG. 11D) p65 and (FIG. 11E) Foxo1/3 phosphorylation in the TA skeletal muscles of mice bearing C-26 tumors and treated with rAAV6:Smad7 (*, p<0.02 vs. control, n=5-11, two-way ANOVA).

SEQUENCE LISTING

Figure 1A:
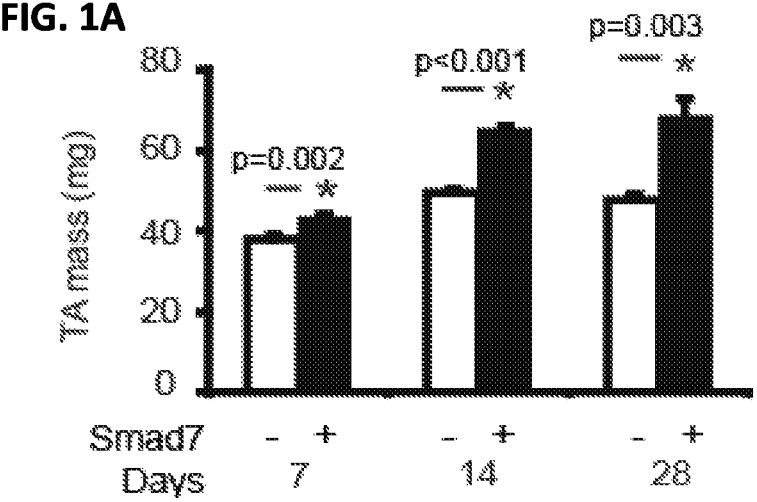
FIGS. 1A-1I show, according to particular aspects, increasing expression of Smad7 promotes skeletal muscle hypertrophy.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOs: 1 and 2 are representative forward and reverse primers used to detect activin A (F: GGAGTGT-GATGGCAAGGTCAACA, R: GTGGGCACACAG-CATGACTTA).

SEQ ID NOs: 3 and 4 are representative forward and reverse primers used to detect myostatin (F: CCCAGAGGTTCAGCAGGCCCT, R: TCAT-GAGCACCCACAGCGGTC).

SEQ ID NO: 5 is the sequence of Smad7 AAV vector pAAV-MCS_smad7stp 081809.cep.

I. Abbreviations
AAV adeno-associated virus
ActRIIB Type IIB activin receptor
ALK activin like kinase
IEE integration efficiency element
ITR inverted terminal repeat
CTGF connective tissue growth factor
COL1A1 collagen type 1a1
FN fibronectin
ND not different
ORF open reading frame
PAI1 plasminogen activator inhibitor 1
rAAV recombinant AAV
SEM standard error of the mean
TA tibialis anterior
TRS terminal resolution site
WT wild type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently eleven recognized serotypes of AAV (AAV1-AAV11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

Infective: A virus or vector is "infective" when it transduces a cell, replicates, and (without the benefit of any complementary virus or vector) spreads progeny vectors or viruses of the same type as the original transducing virus or vector to other cells in an organism or cell culture, where the progeny vectors or viruses have the same ability to reproduce and spread throughout the organism or cell culture. Thus, for example, a nucleic acid encoding an adenoviral particle is not infective if the nucleic acid cannot be packaged (e.g. if the adenoviral particle lacks a packaging site), even though the nucleic acid can be used to transfect a cell. Similarly, an adenoviral nucleic acid packaged by an adenoviral particle is not infective if it does not encode the adenoviral capsid proteins in which it is packaged.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Mammal: This term includes both human and non-human mammals. Similarly, the term "subject" includes both human and veterinary subjects.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Packaging cell: A cell that provides packaging functions in trans for a gene introduced into a cell with a transfer vector, but which does not encapsidate its own genome.

Packaging Vector: Packaging vector nucleic acids lack the nucleic acids necessary for packaging of a DNA corresponding to the packaging vector nucleic acid into an adenoviral capsid. That is, packaging vector nucleic acids are not themselves encapsidated in the viral particles which they encode, i.e. they are not infective. The packaging vector optionally includes all of the components necessary for production of viral particles, or optionally includes a subset of the components necessary for viral packaging. For instance, a packaging cell may be transformed with more than one packaging vector, each of which has a complementary role in the production of an adenoviral particle.

Two (or more) adenoviral-based packaging vectors are "complementary" when they together encode all of the functions necessary for adenovirus packaging, and when each individually does not encode all of the functions necessary for packaging. For example, when two vectors transduce a single cell and together they encode the information for production of adenovirus packaging particles, the two vectors are "complementary." The use of complementary vectors increases the safety of any packaging cell made by transformation with a packaging vector by reducing the possibility that a recombination event will produce an infective virus.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as cancer) or a symptom associated with a disease (such as cancer cachexia) refers to inhibiting the full development of a disease or symptom. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule (such as a recombinant nucleic acid molecule encoding Smad7) has been packaged.

Sequence Identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-410, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Smad (SMAD) proteins: A family of transcription factors found in vertebrates, insects and nematodes. SMADs are intracellular proteins that transduce extracellular signals ligands to the nucleus, where they activate downstream gene transcription. Generally, SMADs form a trimer of two receptor-regulated SMADs and one co-SMAD.

Smad7 is homolog 7 of the *Drosophila* gene Mothers against decapentaplegic. It is a TGFβ type 1 receptor antagonist. It blocks TGFβ1 and activin associating with the receptor, blocking access to SMAD2. It is an inhibitory SMAD (I-SMAD) and is enhanced by SMURF2.

Representative nucleotide sequences encoding Smad7 include: human (NM_005904.3); mouse/murine (NM_001042660.1); cattle/bovine (NM_001192865.1); dog/canine (XM_005623131.1); pig/porcine (NM_001244175.1); sheep/ovine (XM_012120929.1); and horse/equine (XM_001499061.5). The content of these GenBank accession numbers is hereby incorporated by reference as available on Apr. 22, 2016.

Subject: Living multi-cellular vertebrate organisms, a category that includes human and non-human mammals. By way of example, the Smad7 sequence used in a therapeutic composition or treatment described herein may be tailored to match the species being treated therewith (e.g., a human sequence used in treatment of human subjects; a dog sequence on dog subjects, and so forth).

Synthetic: Produced by artificial means in a laboratory, for example a synthetic nucleic acid can be chemically synthesized in a laboratory.

Therapeutically effective amount: A quantity of a specified pharmaceutical or therapeutic agent (e.g. a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Treating or treatment: Includes the application or administration of a composition to a subject, or application or administration of a composition to a cell or tissue from a subject has symptoms of muscle wasting, such as cancer cachexia, with the purpose of curing, healing, alleviating, relieving, altering, remedying, ameliorating, improving, or affecting the disease or condition, the symptom of the disease or condition, or the risk of the disease or condition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

DETAILED DESCRIPTION OF EXEMPLARY ASPECTS

The loss of muscle mass and strength is a leading predictor of poor prognosis in many cancer patients (Tisdale, Physiol Rev 89, 381-410, 2009; Fearon et al., Cell metabolism 16, 153-166, 2012; Dodson et al., Annu Rev Med 62, 265-279, 2011). We demonstrate herein for the first time that a gene therapy-based intervention targeting ActRIIB signaling (Llovera et al., Biochem Biophys Res Commun 221, 653-655, 1996; Llovera et al., Mol Cell Endocrinol 142, 183-189, 1998; Cai et al., Cell 119, 285-298, 2004; Wyke et al., Br J Cancer 91, 1742-1750, 2004; Watchorn et al., Int J Oncol 27, 1105-1111, 2005; Wyke & Tisdale, Br J Cancer 92, 711-721, 2005) is an effective means of preventing the muscle wasting associated with tumor progression. As gene-based therapies are currently being developed for neuromuscular disorders and non-muscle-diseases (Mingozzi & High, Nat Rev Genet 12, 341-355, 2011), we contend that the strategy described here could translate to interventions capable of reducing morbidity and mortality associated with muscle wasting in the setting of cancer cachexia, and other diseases with excessive ActRIIB signaling.

According to particular aspects, given that elevated circulating concentrations of myostatin and activin can cause skeletal muscle atrophy, and have been associated with cancer, aging, and conditions of chronic illness where muscle wasting occurs (Fearon et al., Cell metabolism 16, 153-166, 2012; Zimmers et al., Science 296, 1486-1488, 2002; Coerver et al., Mol Endocrinol 10, 534-543, 1996; Harada et al., J Clin Endocrinol Metab 81, 2125-2130, 1996; Costelli et al., Eur J Clin Invest 38, 531-538, 2008; Heineke et al., Circulation 121, 419-425, 2010; Penna et al., PLoS One 5, e13604, 2010; Ju & Chen, et al., Respir Med 106, 102-108, 2012; Otani et al., Gynecol Oncol 83, 31-38, 2001; Seder et al., Neoplasia 11, 388-396, 2009; Wildi et al., Gut 49, 409-417, 2001; Han et al., Int J Biochem Cell Biol, 45:2333-2347, 2013), considerable effort has been invested in developing interventions that can mitigate the harmful effects of excessive ActRIIB signaling, by targeting the responsible ligands in the circulation (Fearon et al., Cell metabolism 16, 153-166, 2012; Benny Klimek et al., Biochem Biophys Res Commun 391, 1548-1554, 2010; Zhou et al., Cell 142, 531-543, 2010).

However, the feasibility of therapies based on such ligand traps remains in question, because of potential side effects associated with inhibiting pleiotropic ligands at the extracellular level (Massague, Nat Rev Mol Cell Biol 13, 616-630, 2012). To circumvent these problems, we investigated whether inhibiting ActRIIB signaling within muscle fibers represents a strategy to inhibit wasting without binding ligands directly. We found that muscles treated with rAAV6:Smad7 were protected from atrophy when challenged by experimental over-expression of myostatin and activin A. We also determined that rAAV6:Smad7 could ameliorate systemic muscle wasting independent of tumor burden and persistently elevated circulating levels of pro-cachectic ligands. These results demonstrate the utility of our approach for dissociating the activity of key intracellular signaling processes involved in maintaining muscle mass from the effects of ligands that utilize these pathways to promote muscle wasting. Moreover, the efficacy of rAAV6:Smad7 is virtually identical to that described for a soluble ActRIIB ligand trap in cachectic mice (Zhou et al., Cell 142, 531-543, 2010), yet rAAV6:Smad7 is more specific to striated muscle and, based on our results, less likely to produce off-target effects.

According to particular aspects, most importantly, none of the off-target signs associated with ACE-031 (a peptibody ligand trap largely composed of the extracellular domain of ActRIIB) was detected in any mouse treated with rAAV6:Smad7. Nor was Smad7 expression in non-muscle tissues or markers of Smad7 bioactivity. The latter include internal markers such as changes in lung weight and morphology or evidence of compromised microvasculature as well as readily apparent external markers such as bruising on ears, nose and tails. Although such markers could presumably present intermittently, the combined specificity of our approach along with the lack of any detectable HHT signs, strongly suggest that rAAV6; Smad7 is a safe and possibly more efficacious alternative to ActRIIB ligand traps.

According to particular aspects, mechanistically, ActRIIB signaling can promote muscle catabolism by repressing synthesis of muscle proteins, and promoting protein degradation (Amirouche et al., Endocrinology 150, 286-294, 2009; Trendelenburg et al., Am J Physiol Cell Physiol 296, C1258-1270, 2009; Durieux et al., Endocrinology 148, 3140-3147, 2007; Lokireddy et al., Mol Endocrinol 25, 1936-1949, 2011). Our studies described herein demonstrate that over-expression of Smad7 increases S6K/S6RP signaling associated with protein synthesis, but not by mechanisms that are contingent upon activation of Akt and mTOR. We also observed that over-expression of Smad7 in cachectic muscles reduces the transcription of the E3 ubiquitin ligases MuRF1 and Atrogin-1, the activity of which facilitate proteasomal degradation in skeletal muscle. The effects of Smad7 on both anabolic and catabolic signaling were dependent upon inhibition of Smad2/3 phosphorylation, but Smad7 readily prevented excessive Smad2/3 phosphorylation associated with increased myostatin and activin levels in all of the mouse models studied. These results support the hypothesis that increased expression of Smad7 represents a potent method to inhibit excessive ActRIIB:ActRI-mediated Smad2/3 phosphorylation, which otherwise contributes to significant muscle catabolism.

According to particular aspects, the amelioration of skeletal muscle atrophy in tumor bearing mice administered rAAV6:Smad7 compares favorably with the previously reported anti-catabolic effects of repeatedly treating similar mouse models with soluble ActRIIB (Zhou et al., Cell 142, 531-543, 2010), which prolonged survival in spite of tumor progression. Similar to studies where cachectic mice received soluble ActRIIB (Zhou et al., Cell 142, 531-543, 2010), tumor bearing mice treated with a systemic administration of rAAV6:Smad7 as described herein did not demonstrate enhanced preservation of fat mass compared with sham-treated tumor-bearing counterparts. Ameliorating lipolysis in cachexia may be more effectively achieved by jointly targeting other cachexia-associated cytokines, such as TNFα (Llovera et al., Biochem Biophys Res Commun 221, 653-655, 1996; Llovera et al., Mol Cell Endocrinol 142, 183-189, 1998). However, results indicate conservation of lean mass should be the primary goal of interventions aimed at prolonging survival (Fearon et al., *Cell Metabolism* 16, 153-166, 2012; Lee & Glass, *Skelet Muscle* 1, 2, 2011; Zhou et al., *Cell* 142, 531-543, 2010).

According to particular aspects, intravenous administration of rAAV6:Smad7 also prevented cardiac atrophy in tumor-bearing mice, as rAAV6 vectors via the circulation can transduce cardiac muscle. Increased expression of myostatin and activin A has been associated with heart disease (Heineke et al., *Circulation* 121, 419-425, 2010; Yndestad et al., *Circulation* 109, 1379-1385, 2004; Rodgers et al., *J Physiol* 587, 4873-4886, 2009), and physiological hypertrophy and enhanced cardiac contractility and $Ca^{2+}$ handling all occur in myostatin-null hearts (Rodgers et al., *J Physiol* 587, 4873-4886, 2009; Jackson et al., *J Endocrinol* 213, 263-275, 2012; Jackson et al., *Endocrinology* 155, 1771-1785, 2014), which are comparatively protected with insult (Bish et al., *PLoS One* 5, e10230, 2010; Artaza et al., *J Endocrinol* 194, 63-76, 2007). Therefore, systemic administration of rAAV: Smad7 vectors with tropism for the myocardium also constitutes an attractive prospect for repressing ActRIIB-mediated atrophic signaling in the heart and to preserve cardiac performance in cachectic patients.

Because ActRIIB is expressed in many non-muscle tissues and several TGFβ superfamily ligands engage this receptor to exert diverse tissue-specific actions, ligand trapping approaches pose significant risk for causing off-target effects (Koncarevic et al., *Endocrinology* 153, 3133-3146, 2012). Data presented herein introduce rAAV6:Smad7 as a novel approach for attenuating ActRIIB signaling preferentially in striated muscle (Gregorevic et al., *Nat Med* 10, 828-834, 2004; Gregorevic et al., *Nat Med* 12, 787-789, 2006). The inclusion of tissue-specific promoters capable directing Smad7 expression uniquely in skeletal and/or cardiac muscle would further enhance specificity and have already been developed (Salva et al., *Mol Ther* 15, 320-329, 2007). Their inclusion could potentially improve specificity even more by providing greater control and possibly more robust Smad7 expression. Additional studies are therefore advocated to optimize our approach and to determine its efficacy in other conditions of muscle wasting or even heart failure.

AAV belongs to the family Parvoviridae and the genus *Dependovirus*. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008).

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008).

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev* 21(4):583-593, 2008).

Methods for producing rAAV suitable for gene therapy are well known in the art (see, for example, U.S. Patent Application Nos. 2012/0100606; 2012/0135515; 2011/0229971; and 2013/0072548; and Ghosh et al., *Gene Ther* 13(4):321-329, 2006), and can be utilized with the recombinant nucleic acid molecules, vectors and methods disclosed herein.

The following examples are provided to illustrate certain particular features and/or embodiments. These examples should not be construed to limit the disclosure to the particular features or embodiments described.

Example 1: Materials And Methods

Antibodies—All antibodies used were obtained from Cell Signaling (Danvers, Mass.), except for antibodies against Smad7 (Imgenex, San Diego, Calif.), pSmad3 (Epitomics, Burlingame, Calif.) and GAPDH (Santa Cruz Biotechnology, Dallas, Tex.).

Figure 12:
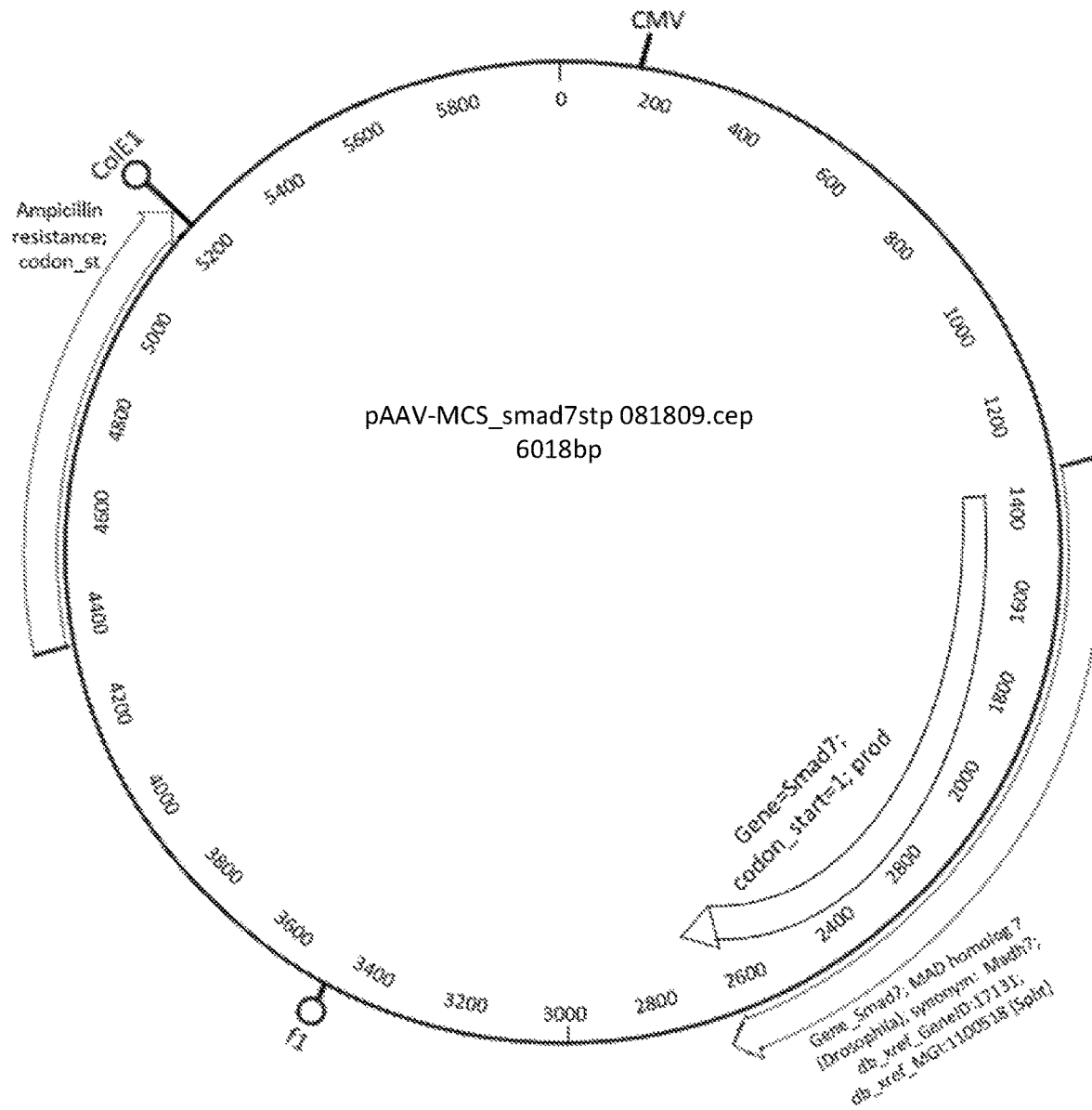
FIG. 12 shows a map of a Smad7 AAV vector, pAAV-MCS_smad7stp 081809.cep; the corresponding sequence is provided in SEQ ID NO: 3 (6108 base pairs).

Production of rAAV6 vectors—cDNA constructs encoding for Smad7 GenBank Reference #NM_001042660.1), which was PCR amplified from a mouse cDNA library, activin A, myostatin and Smad3-CA (all synthesized by GenScript, Piscataway, N.J.) were cloned into a rAAV expression plasmid consisting of a CMV promoter/enhancer and SV40 poly-A region flanked by AAV2 terminal repeats, using standard cloning techniques. The sequence of the resultant vector is provided in SEQ ID NO: 5; a map is provided in FIG. 12. Transfection of these plasmids with the pDGM6 packaging plasmid (which contains the AAV6 cap genes, AAV2 rep genes, and also adenovirus helper genes; Gregorevic et al., *Nat. Med.* 10, 828-834, 2004; incorporated herein by reference) into HEK293 cells generated type-6 pseudotyped viral vectors that were harvested and purified (Gregorevic et al., *Nat Med* 10, 828-834, 2004). Briefly, HEK293 cells were plated at a density of 3.2-3.8×10$^6$ cells on a 10 cm culture dish, 8-16 hours prior to transfection with 10 µg of a vector-genome-containing plasmid and 20 µg of the packaging/helper plasmid pDGM6, by means of the calcium phosphate precipitate method to generate pseudotype 6 vectors. Seventy-two hours after transfection, the media and cells were collected and homogenized through a microfluidizer (Microfluidics, Westwood, Mass.) prior to 0.22 µm clarification (Merck Millipore, Billerica, Mass.). The vector was purified from the clarified lysate by affinity chromatography over a heparin affinity column (HITRAP™, GE Healthcare, Pittsburgh, Pa.), and ultra-centrifuged overnight prior to re-suspension in sterile physiological Ringer's solution. The purified vector preparations were titered with a customized sequence-specific PCR-based reaction (Life Technologies, Grand Island, N.Y.).

Animal Experiments—All experiments were conducted in accordance with the relevant codes of practice for the care and use of animals for scientific purposes (National Institutes of Health, USA, 1985; the National Health & Medical Council of Australia, 2013).

For local vector delivery, mice were anesthetized deeply with isoflurane, or a mixture of ketamine (100 mg/kg) and xylazine (10 mg/kg; intraperitoneal injection, VM Supplies, Chelsea Heights, VIC, AU). 1-10×10$^9$ vector genomes of a given vector were administered in 30 µL of Hank's buffered saline solution (HBSS) directly into the anterior compartment of the hind limb, which is occupied by the tibialis anterior (TA) and extensor digitorum longus (EDL) muscles. Control-injections of the contralateral limb used a vector lacking a functional gene (rAAV6:MCS) (Han et al., *Int J Biochem Cell Biol*, 45:2333-2347, 2013). For systemic delivery studies, 3-5×10$^{12}$ vector genomes were administered in a 200 µL volume of HBSS via the tail vein. For rapamycin experiments, rapamycin was dissolved overnight in a solution containing 0.2% carboxymethylcellulose sodium salt (Sigma, St. Louis, Mo.) and 0.25% polysorbate-80 (Sigma, St. Louis, Mo.) in water, as described previously (Bourdeau et al., *Am J Pathol* 156, 911-923, 2000). In these experiments, mice received 2 mg/kg/day of rapamycin (Calbiochem®, Merck Millipore, Darmstadt, Germany) or vehicle as a daily intraperitoneal injection commencing 3 hours prior to rAAV6:Smad7 injection and continuing for 14 days inclusive. For tissue harvest, mice were humanely killed via a cervical dislocation, and the muscles rapidly excised and weighed before subsequent processing. Implantation of C-26 derived tumor tissue was carried out using CD2F1 or BALB/c mice. Cells or tissue were implanted into the flank of the back as described previously (Bourdeau, et al., *Trends Cardiovasc Med* 10, 279-285, 2000; Bourdeau et al., *Am J Pathol* 158, 2011-2020, 2001). Briefly, cells were passaged immediately prior to implantation and reconstituted in 10% DMEM media, while tumor pieces were thawed from liquid nitrogen. Cells, or 1 mm$^3$ pieces, were then implanted, using a trocar needle, through a small incision in the flank of the back and mice were terminated 21 days later. Fat, lean and total body masses of inhibin-a null mice were analyzed using Echo-MRI technology (Echo Medical Systems, Houston, Tex.).

Real Time PCR—Total RNA was collected from TA muscles cells using Trizol (Life Technologies, Thermo Fisher Scientific, Waltham, Mass.). 500-1000 ng of RNA was reverse transcribed using the High Capacity RNA-to-cDNA kit (Life Technologies). cDNA for Smad7, Foxo1, Foxo3, MAFbx and MuRF1 was then analyzed by RT-PCR using Taqman™ polymerase assay on demand kits and detection software (Life Technologies). 18S was used to standardize cDNA concentrations. Data were analyzed using the $\Delta\Delta C_T$ method of analysis. Activin A (F: GGAGTGT-GATGGCAAGGTCAACA, SEQ ID NO: 1; R: GTGGGCACACAGCATGACTTA, SEQ ID NO: 2) and myostatin (F: CCCAGAGGTTCAGCAGGCCCT, SEQ ID NO: 3; R: TCATGAGCACCCACAGCGGTC, SEQ ID NO: 4) were detected via SYBR® Green real-time PCR method of detection.

ELISA—The concentration of activin A in mouse serum was determined by ELISA, following the manufacturer's instructions (Oxford Bio-innovations, Oxfordshire, UK), using previously described modifications (Satomi, et al., *Stroke* 34, 783-789, 2003). Serum IL-6 from control and cachectic mice was measured according to the manufacturer's instructions (R&D Systems, Minneapolis, Minn.).

Luciferase experiments—C2C12 cells were either transfected in 24-well plates with 0.35 µg Smad7 plasmid, 0.25 µg pCAGA-luc plasmid or 0.25 µg LacZ plasmid per well using Lipofectamine 2000 (Life Technologies). 16 hours later, media was changed and supplemented with serum from control or C-26 tumor-bearing mice for 24 hours. Cells were then lysed with cell lysis buffer (Promega, Madison, Wis.) and luciferase activity was measured using a luminometer (Berthold, Bad Wildbad, Germany). Luciferase activity is presented as the ratio of pCAGA-luciferase activity to β-galactosidase reporter activity and data are representative of three independent experiments. β-galactosidase was detected using a commercial β-gal detection assay (Promega). Briefly, lysate incubated with 2× β-galactosidase buffer for up to 1 hour at 37° C. β-gal expression was subsequently measured at 420 nm.

Histology—Harvested muscles were placed in OCT cryoprotectant and frozen in liquid nitrogen-cooled isopentane. The frozen samples were subsequently cryosectioned at 10 µm thickness and stained with hematoxylin and eosin to examine morphology. Sections were mounted using DePeX mounting medium (BDH, VWR International, Radnor, Pa.) and images of stained sections were captured using a U-TV1X-2 camera mounted to an IX71 microscope, and a PlanC 10×/0.25 objective lens (Olympus). DP2-BSW acquisition software (Olympus) was used to acquire images. For fiber type analysis, serial transverse cryosections were obtained from the mid-belly of the TA muscles (−20° C., CTI Cryostat; IEC, Needham Heights, Mass.). Sections were stained with: laminin (#L9393, Sigma-Aldrich) for determination of myofiber diameter and cross-sectional area (CSA), and/or N2.261 (developed by Dr. H. M. Blau, obtained from the Developmental Studies Hybridoma Bank developed under the auspices of the NICHD and maintained by The University of Iowa, Department of Biology, Iowa City, Iowa) to assess the percentage of type-I (Torsney et al., *Circulation* 107, 1653-1657, 2003) and type-IIa (Durieux et al., *Endocrinology* 148, 3140-3147, 2007) myosin isoforms respectively. As shown previously (Lokireddy et al., *Mol Endocrinol* 25, 1936-1949, 2011), all non-N2.261 reacting fibers in mouse TA muscles were assumed to represent type IIx/b fibers. Digital images were obtained using an upright microscope with camera (Axio Imager D1, Carl Zeiss, Wrek, Göttingen, Germany), controlled and quantified by AxioVision AC software (AxioVision AC Rel. 4.7.1, Carl Zeiss). The minimum Feret's diameter and myofiber area was determined using ImageJ software (National Institutes of Health, Bethesda, Md.) by measuring at least 500 myofibers per mouse TA muscle and at least three mice were used per group to quantify these variables.

Western blotting—TA muscles were homogenized in RIPA-based lysis buffer (Merck Millipore) with COMPLETE™ EDTA-free protease and phosphatase inhibitor cocktails (Roche, Basel, Switzerland). Lysis was followed by centrifugation at 13000 g for 10 minutes at 4° C. and samples were denatured for 5 minutes at 95° C. Protein concentration was determined using a Pierce protein assay kit (Thermo Scientific, Rockford, Ill.). Protein fractions were subsequently separated by SDS-PAGE using pre-cast 4-12% Bis-Tris gels (Life Technologies), blotted onto nitrocellulose membranes (Bio-Rad, Hercules, Calif.) and incubated with the appropriate antibody overnight. Quantifications of labeled Western blots were performed using ImageJ pixel analysis (National Institutes of Health), and data were normalized to a control value of 1. Densitometric analyses of Western blots are presented as band density normalized to the loading control, and are representative of at least three independent experiments.

Akt kinase assay—A non-radioactive Akt kinase assay (Cell Signaling Technology, Danvers, Mass.) was performed according to the manufacturer's instructions. TA muscles injected with rAAV6:Smad7 or rAAV6:MCS were collected, homogenized and protein samples were then subjected to overnight immunoprecipitation using an antibody against the Ser473 site of Akt. A portion of the protein lysate was set aside as the total cell lysate. Immunoprecipitated beads were then pelleted, washed and incubated with kinase buffer, ATP and a GSK3α fusion protein for 30 minutes at 30° C. The reaction was then inactivated and samples were analyzed by Western blotting. Akt kinase activity was standardized against total Akt levels.

Ex vivo protein synthesis—EDL muscles were removed with intact tendons and pre-incubated for 30 minutes in 2.0 mL of warmed (30° C.) modified Kreb's-Henseleit buffer (KHB), consisting of 4.5% NaCl, 5.75% KCl, 6.1% CaCl2, 10.55% $KH_2PO_4$, 19.1% $MgSO_4.7H_2O$, 16% v/v $NaHCO_3$ (pH=7.4) supplemented with 4% bovine serum albumin (Bovostar, Bovogen, East Keilor, VIC, Australia), and 5 mM glucose before gassing with 95:5% $O_2:CO_2$. The intracellular protein pool was labeled by transferring EDL muscles to vials containing 2.0 mL of pulse (radioactive) buffer comprising 5 µCi/mL of 3H-Tyrosine (GE Healthcare) and 500 mM L-Tyrosine in KHB for 1 hour. After labeling, the muscles were rinsed in non-radioactive KHB, dry blotted, weighed, snap frozen in liquid nitrogen and stored at −80° C. The frozen muscles were homogenized in 500 µL of 10% Trichloroacetic acid, and centrifuged at 10,000 g for 15 minutes (4° C.). Pellets corresponding to the insoluble protein fractions were re-suspended in 500 µL of 1 M NaOH and allowed to dissolve overnight at room temperature. To estimate tyrosine incorporation, 100 µL of each re-suspended sample was added to 5 mL of scintillation fluid, and 3H radioactivity measured for triplicates of each sample in a scintillation counter (Beckman Coulter, Brea, Calif.).

Assessment of muscle function—As described previously (Han et al., Int J Biochem Cell Biol, 45:2333-2347, 2013; Lokireddy et al., Mol Endocrinol 25, 1936-1949, 2011) the contractile properties of the mice' TA muscles were assessed in situ, by delivering a series of electrical stimuli to the tibial motor nerve via percutaneous electrodes, and recording tension generated during contraction via a force transducer attached to the distal tendon with surgical silk suture. Mice were anesthetized with sodium pentobarbitone (NEMBUTAL®; 60 mg/kg; Sigma-Aldrich) via intraperitoneal injection prior to testing and were humanely killed via cardiac excision at the conclusion of evaluation, while still anesthetized deeply. At the conclusion of the protocol, muscles were rapidly excised, dissected free of tendon and connective tissue, and weighed.

Statistical Analysis—Statistical differences were assessed across multiple conditions using one-way or two-way ANOVA tests, with the Student-Newman-Keuls post hoc test used for comparisons between the group means. Comparisons between two conditions only utilized the Students' t-test. Differences between groups were reported as statistically significant for values of p<0.05. Data are presented as the mean±SEM.

Example 2: Increasing Expression of Smad7 Promotes Skeletal Muscle Hypertrophy

Figure 1B:
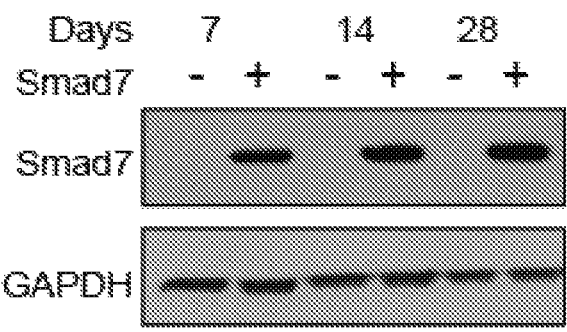
Figure 1C:
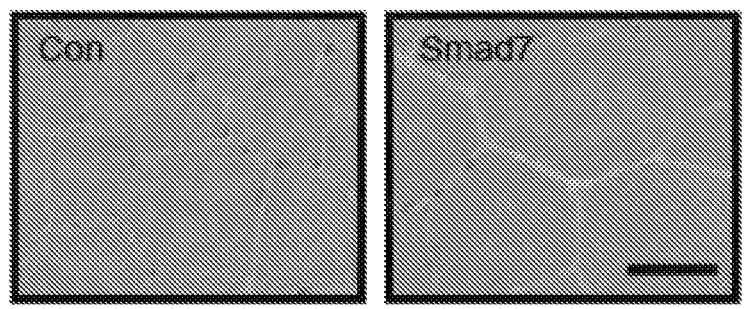
Figure 1D:
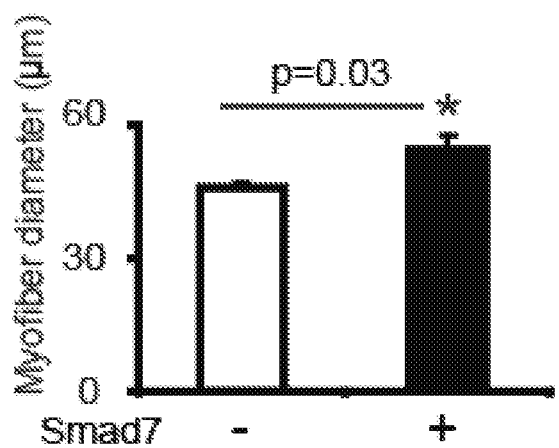
Figure 1E:
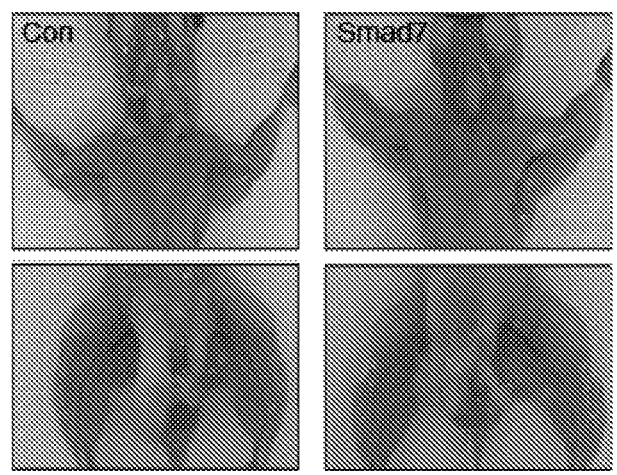
Figure 1F:
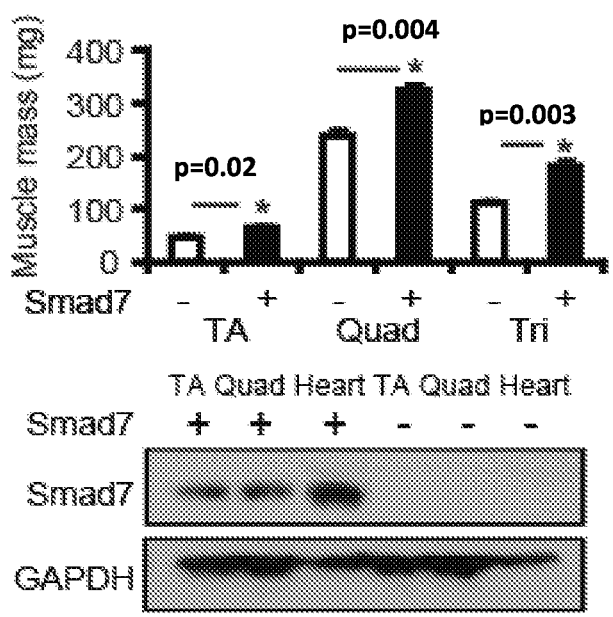
Figure 2A:
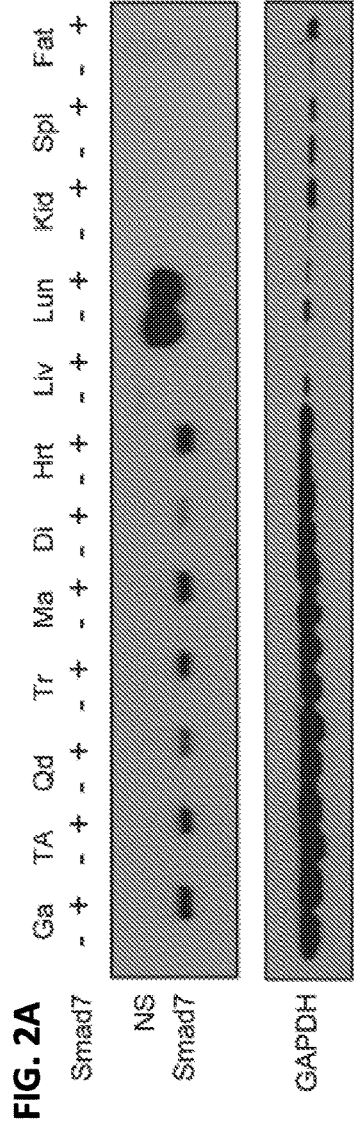
FIGS. 2A-2D show, according to particular aspects, specificity of systemic rAAV6:Smad7 administration and the induction of skeletal muscle hypertrophy.
Figure 2B:
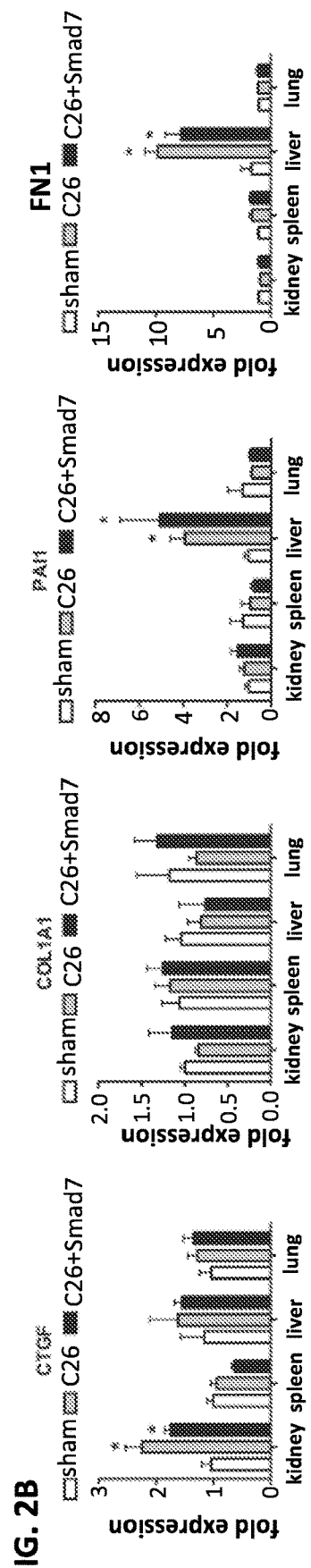
Figure 2C:
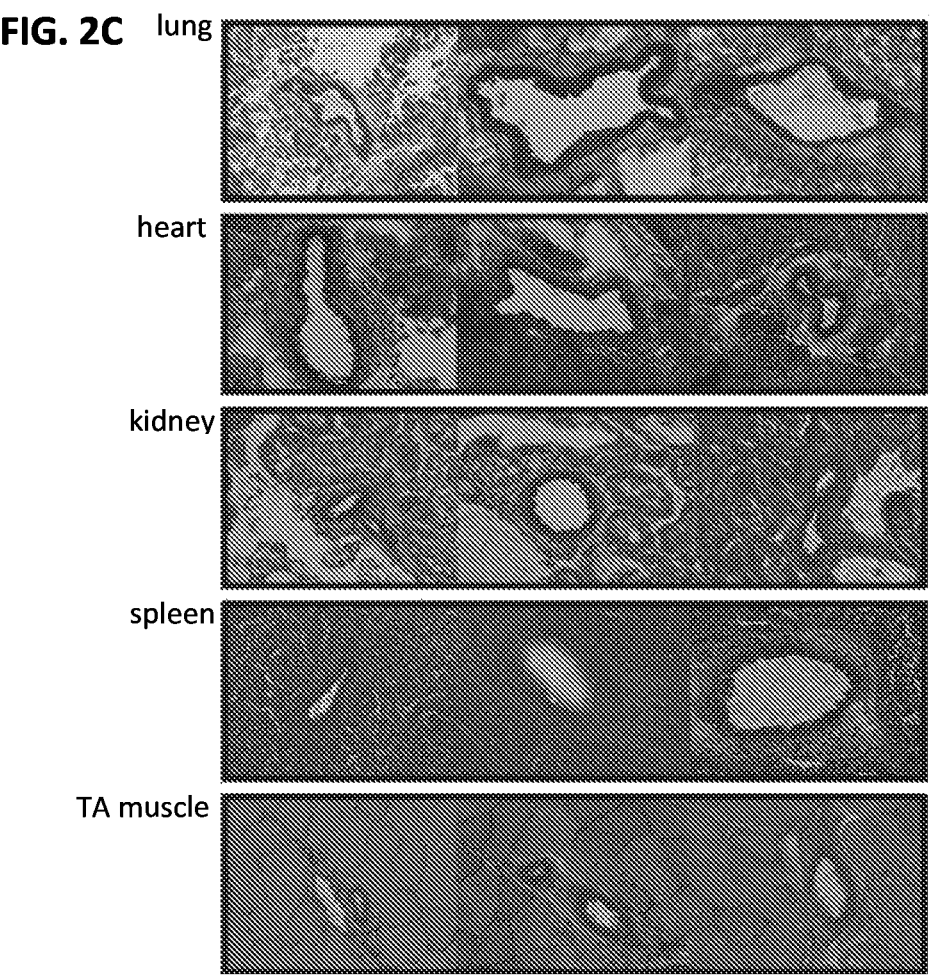
Figure 2D:
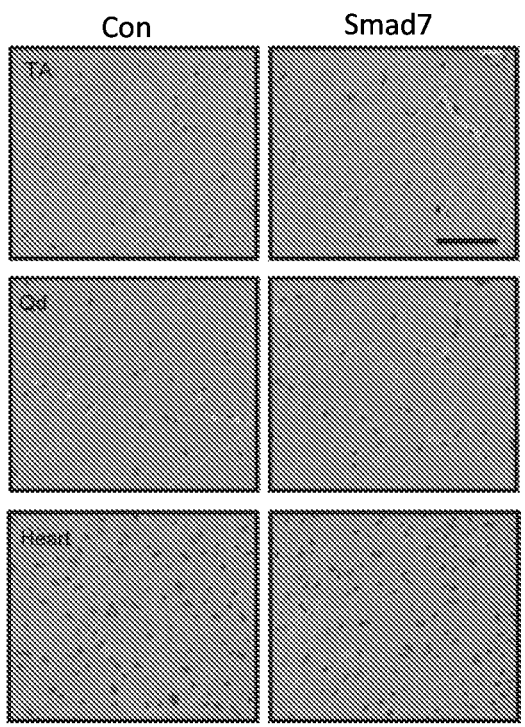

In this example, injection of the tibialis anterior (TA) hind limb muscles of mice with rAAV6 vectors (Gregorevic et al., Nat Med 10, 828-834, 2004; Gregorevic et al., Nat Med 12, 787-789, 2006) carrying a Smad7 expression cassette (rAAV6:Smad7) elicited a ~45% increase in muscle mass within 28 days of injection (FIG. 1A), concomitant with increases in Smad7 protein expression (FIG. 1B) and myofiber diameter (FIG. 1C-1D). Systemic transduction of the musculature of mice via tail vein administration of rAAV6: Smad7 promoted hypertrophy of skeletal muscles body-wide (FIG. 1E-1F). Because rAAV6 vectors display tropism for striated muscle (Gregorevic et al., Curr Opin Mol Ther 6, 491-498, 2004), we subsequently determined that Smad7 protein was readily expressed in striated muscles (FIG. 1F), but not visceral organs or fat, and that the expression of Smad2/3 gene targets (CTGF, COL1A1, PAI1, FN1) was also not altered in a sample of non-muscle tissues including kidney, spleen, liver and lung (FIG. 2A-2B). Blood vessel integrity was also assessed as antagonizing ActRIIb signaling using systemic "ligand traps" can produce signs of heredity hemorrhagic telangiectasia (HHT) (Smith & Lin, Curr Opin Support Palliat Care 7, 352-360, 2013; Bourdeau et al., J Clin Invest 104:1343-1351, 1999). Importantly, systemic rAAV6:Smad7 administration produced no signs of HHT, either in our histological analysis or from gross morphological assessments, although it recapitulated increases in muscle fiber size that were comparable to those obtained via intramuscular injection (FIG. 2C-2D).

Figure 1G:
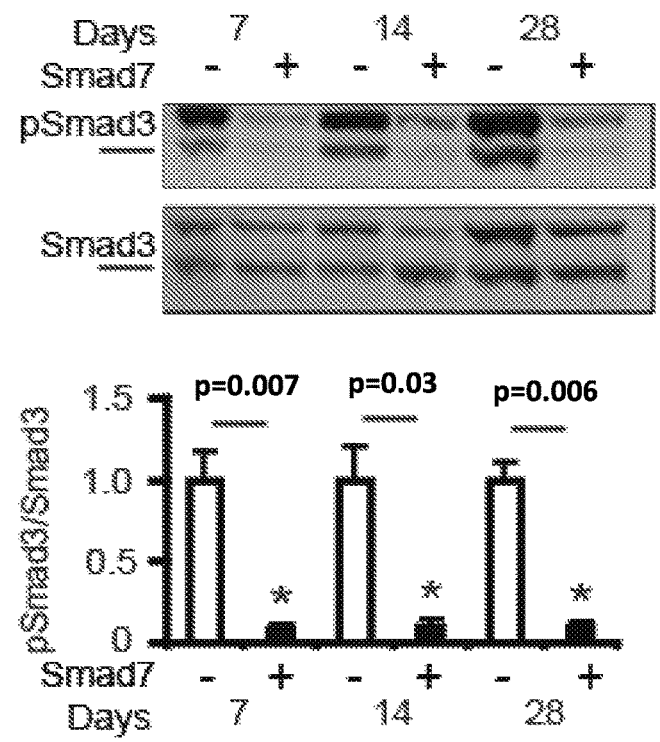
Figure 1H:
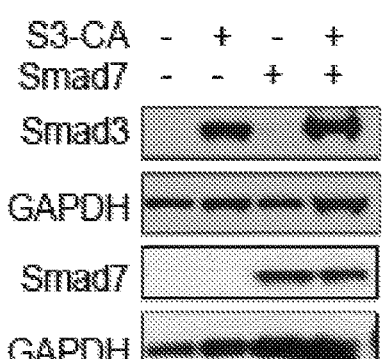
Figure 1H:
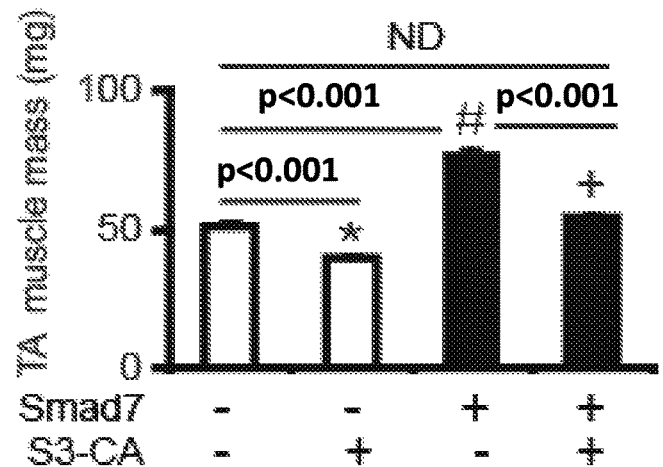
Figure 1I:
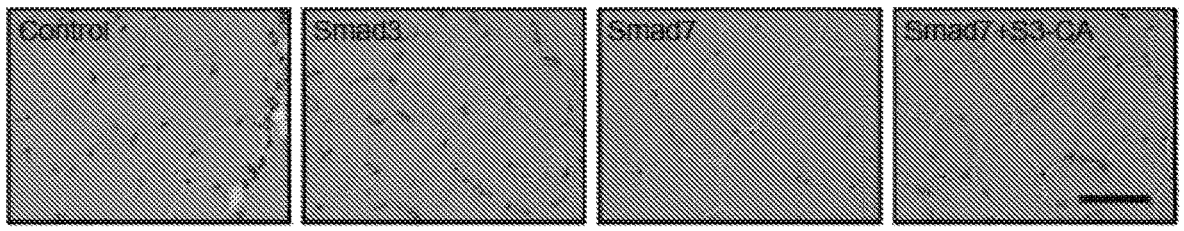
Figure 3A:
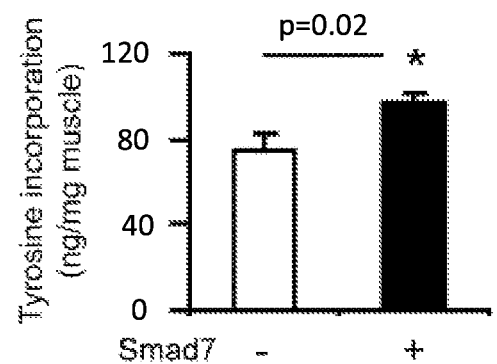
FIGS. 3A-3G show, according to particular aspects, Smad7 regulates skeletal muscle growth independently of Akt and mTOR signaling.
Figure 3B:
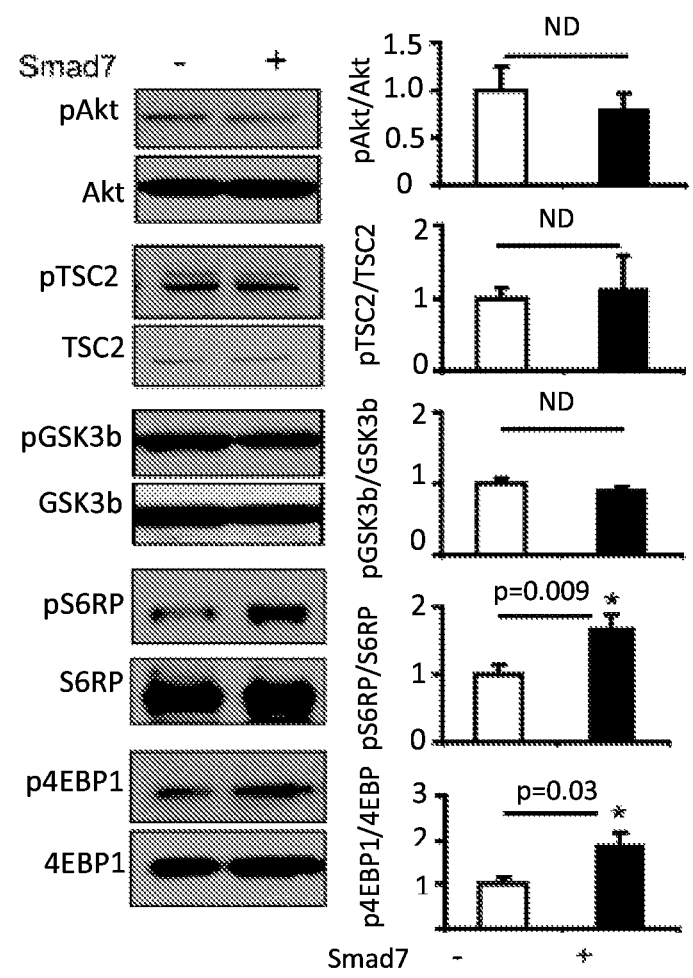
Figure 3C:
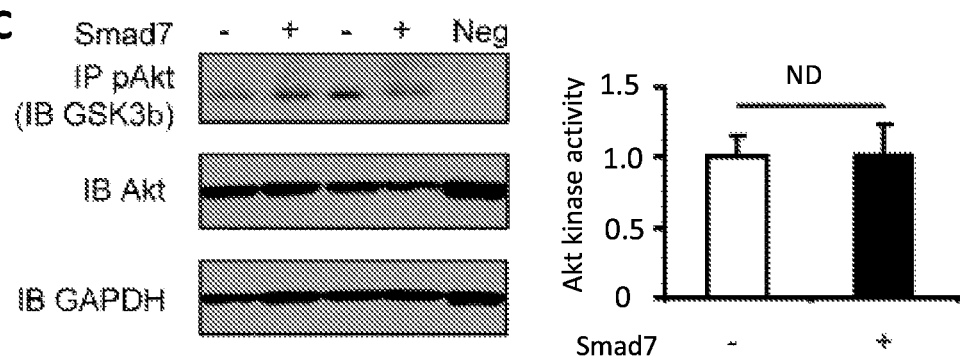
Figure 3D:
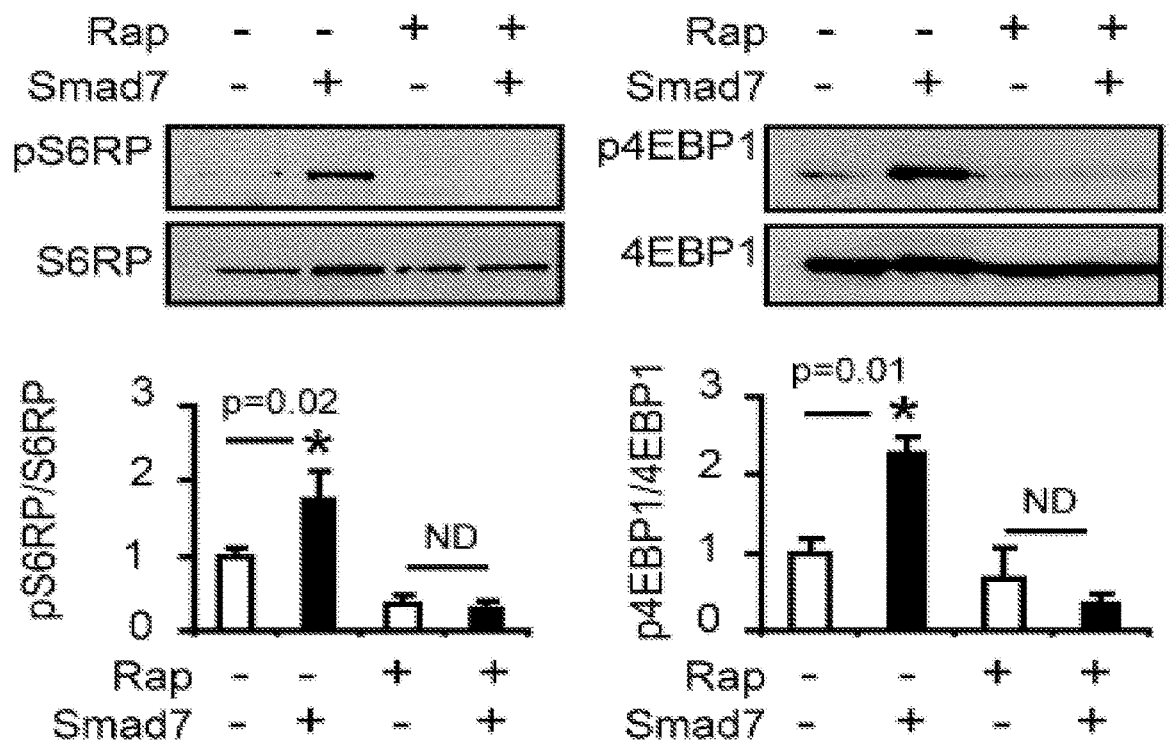
Figure 3E:
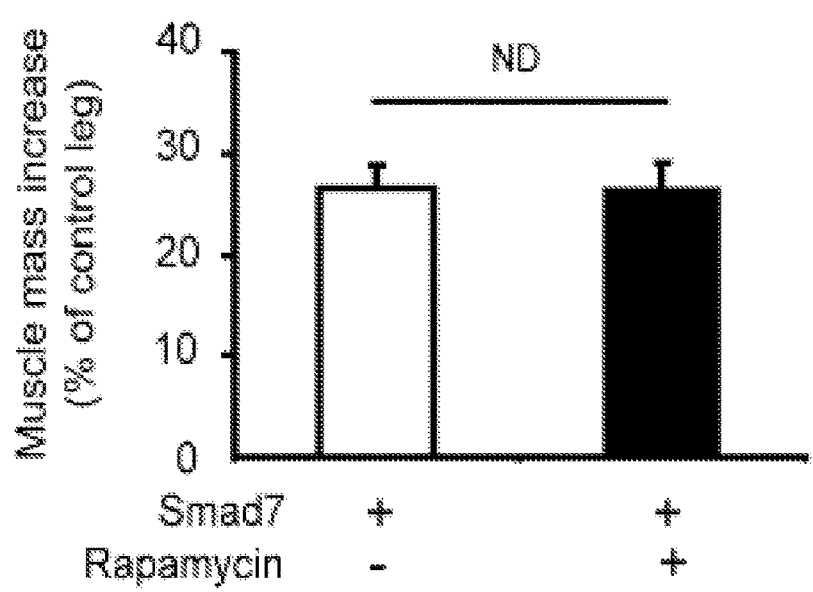
Figure 3F:
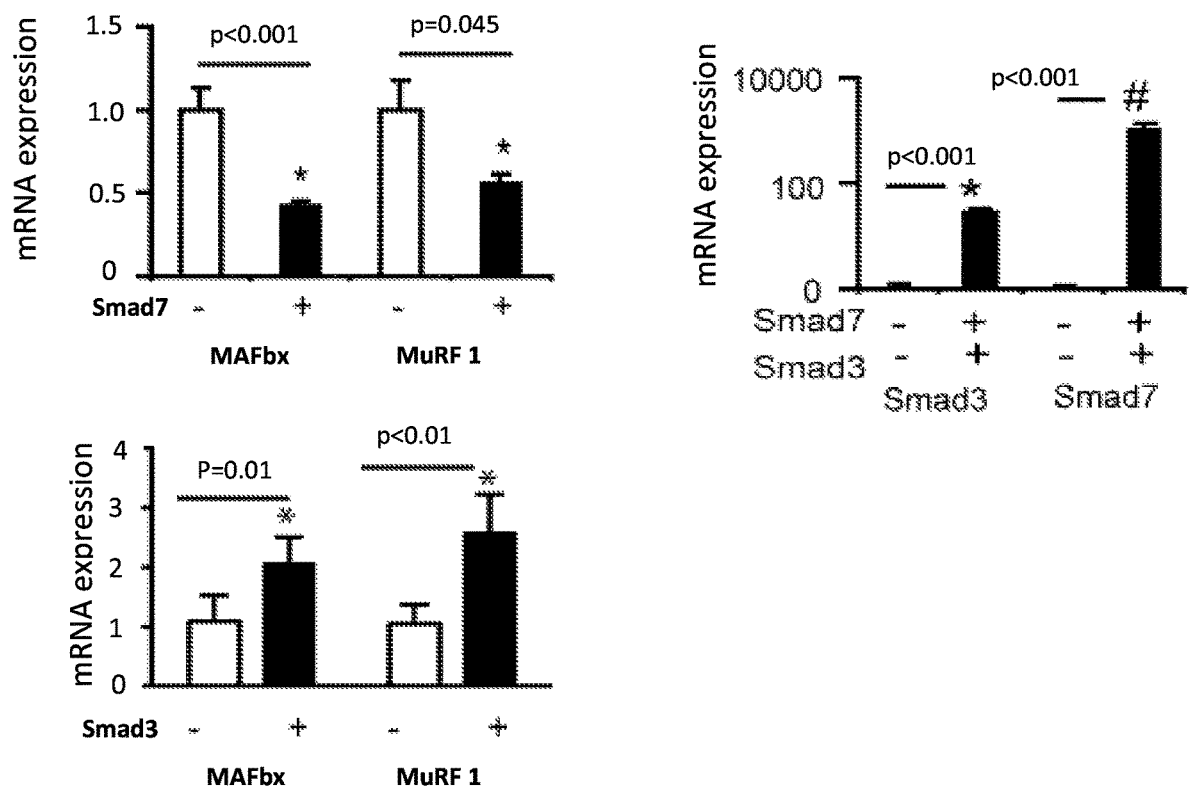
Figure 3G:
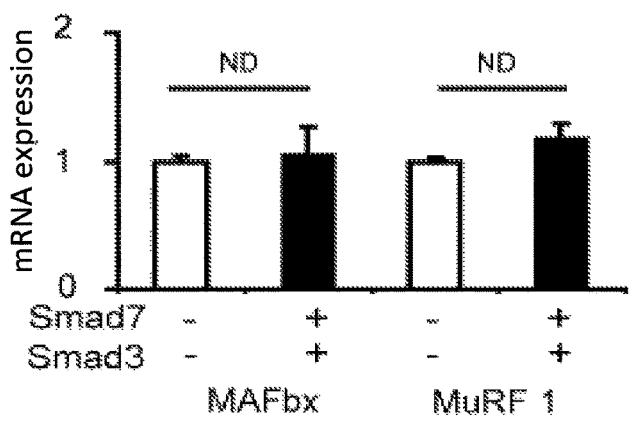

In an additional example, we examined whether the effects of rAAV6:Smad7 administration were attributed to inhibition of Smad2/3 signaling and found that Smad3 S432/435 phosphorylation was potently suppressed in muscles expressing Smad7 (FIG. 1G). Moreover, the effects of Smad7 were abolished in the presence of a constitutively active form of Smad3 (Liu et al., Proc Natl Acad Sci USA 94, 10669-10674, 1997) (CA-Smad3, FIG. 1H-1I). We assessed whether Smad7 expression influenced signaling downstream of Akt and mTOR, a key mechanism promoting protein synthesis (Bodine et al., Nat Cell Biol 3, 1014-1019, 2001). While Smad7 over-expression in muscles increased fractional protein synthesis rates concomitant with increased phosphorylation of targets downstream of mTOR including S6RPS235/236 and 4EBP1T37/46, we could not detect changes to Akt phosphorylation or activity (FIG. 3A-3C) and the administration of rapamycin (an inhibitor of the Akt target, mTOR) did not suppress the hypertrophic response of muscles to rAAV6:Smad7 (FIG. 3D-3E). This is not particularly surprising as we previously demonstrated that inhibiting Smad3 signaling only partially inhibits protein synthesis (Winbanks et al., J Cell Biol 197, 997-1008, 2012) despite ablating mTOR signaling completely. Others have also demonstrated that S6RP can be regulated by upstream MEK/ERK signaling in an mTOR-dependent or -independent manner (Wu et al., *Biochem Biophys Res Commun* 400, 679-683, 2010; Iijima et al., *J Biol Chem* 277, 23065-23075, 2002). We therefore investigated whether the anabolic effects of rAAV6:Smad7 were associated with inhibiting proteolytic mechanisms and found that Smad7 attenuated the basal and Smad3-induced expression of the E3 ubiquitin ligases MuRF1 and MAFbx (FIG. 3F-3G). Thus, Smad7 regulates muscle mass not by enhancing Akt/mTOR signaling, but by suppressing E3 ligase activity and subsequently protein degradation (FIG. 3F), which shifts the balance between protein synthesis and degradation to favor muscle anabolism.

Example 3: Smad7 Prevents Myostatin- and Activin-Induced Muscle Atrophy

In this example, we compared rAAV6:Smad7 efficacy in wild-type and myostatin null (mstn-/-) mice.

Figure 4A:
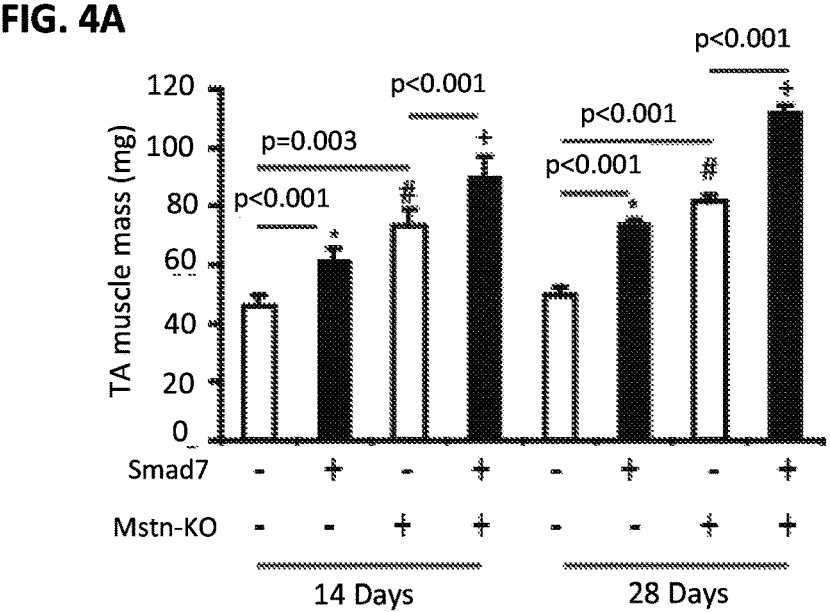
FIGS. 4A-4G show, according to particular aspects, Smad7 prevents myostatin- and activin-induced muscle atrophy.
Figure 4B:
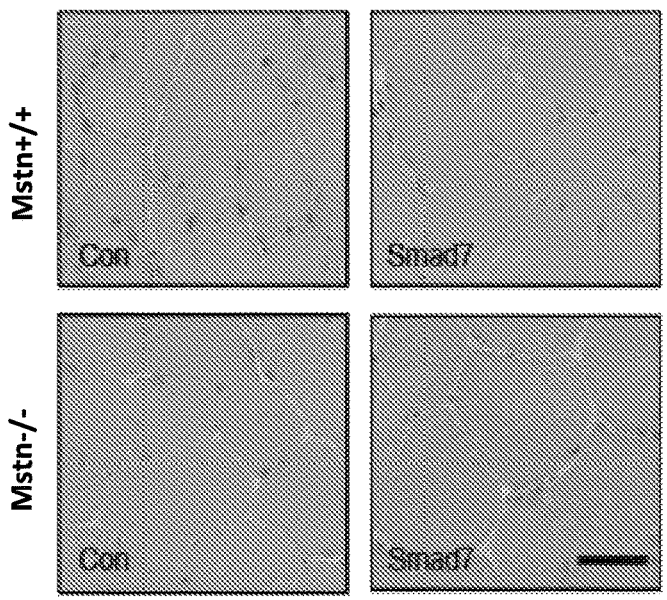
Figure 4C:
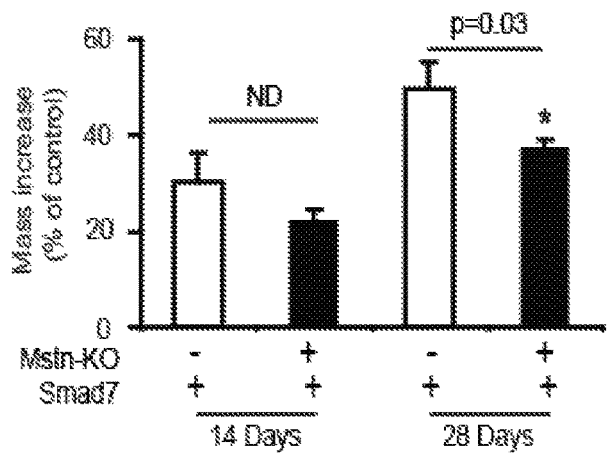
Figure 4D:
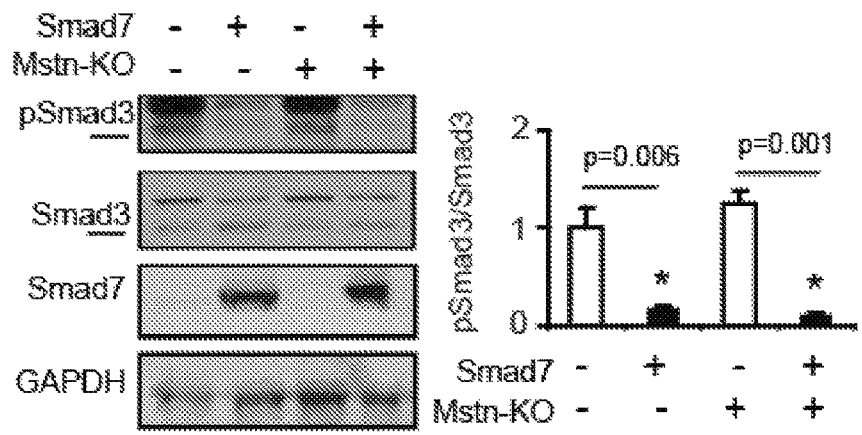
Figure 4E:
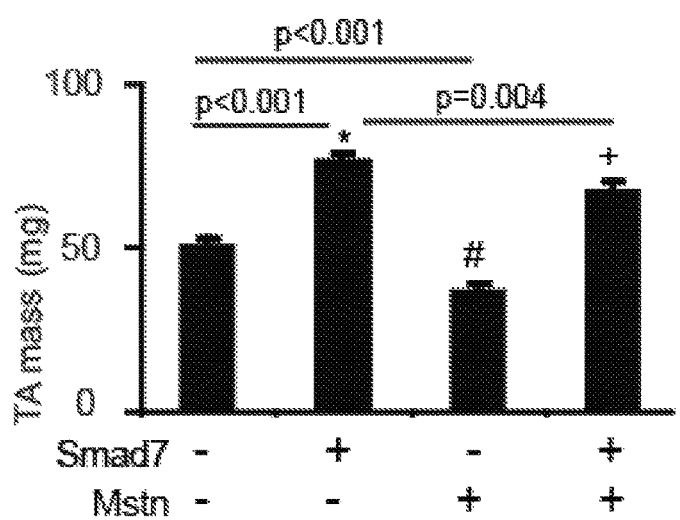
Figure 4F:
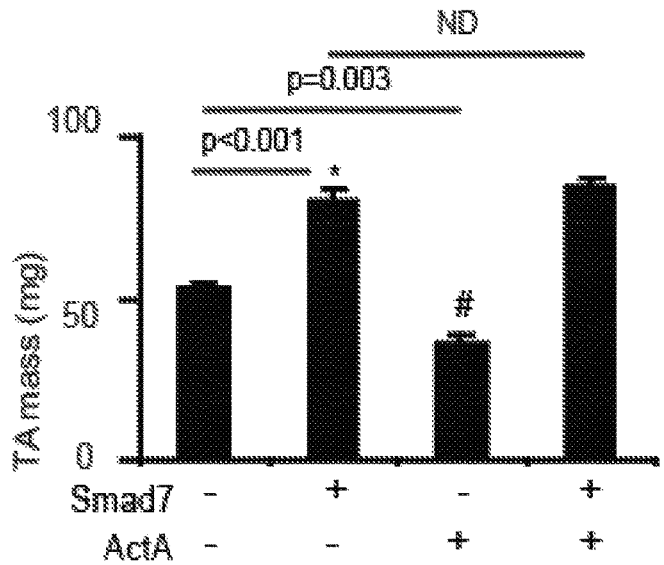
Figure 4G:
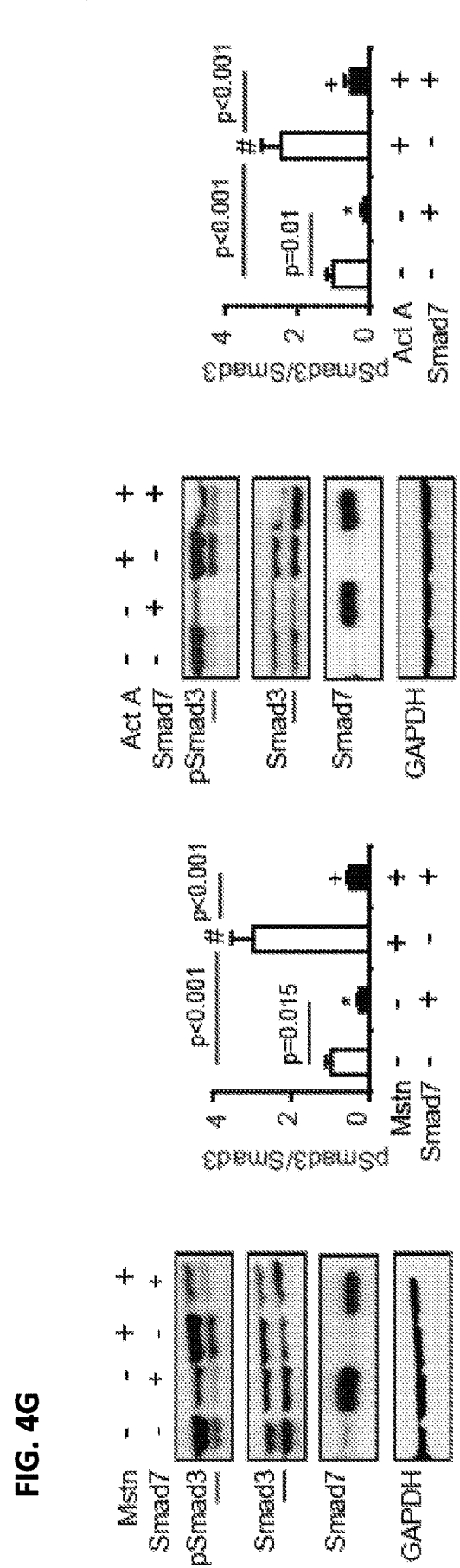
Figure 5C:
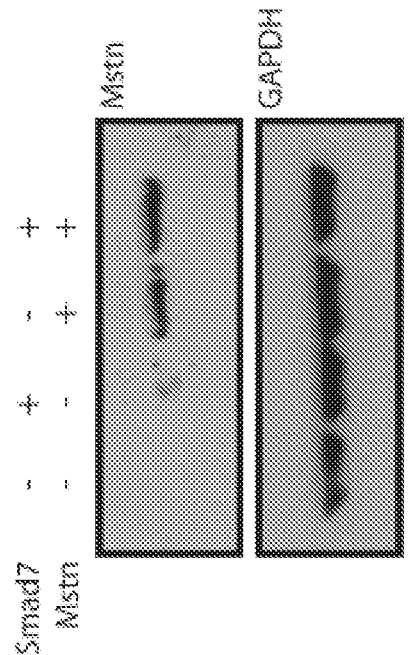
FIGS. 5A-5C show, according to particular aspects, myostatin and Activin A are comparably expressed during single administration or co-administration with rAAV6:Smad7.
Figure 5A:
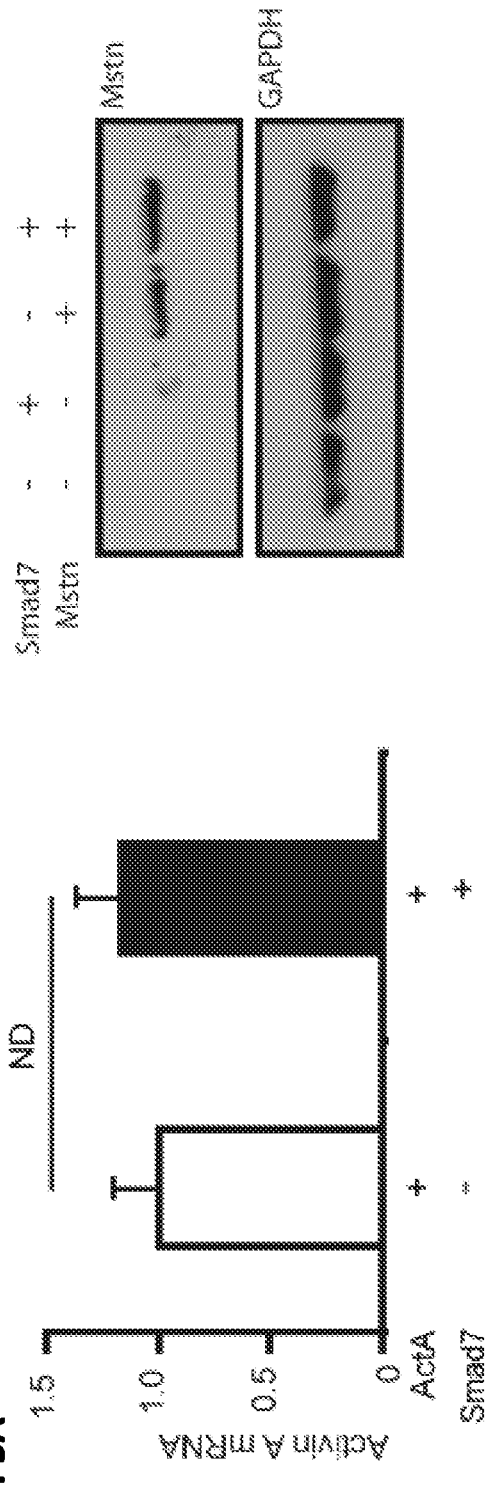
Figure 5B:
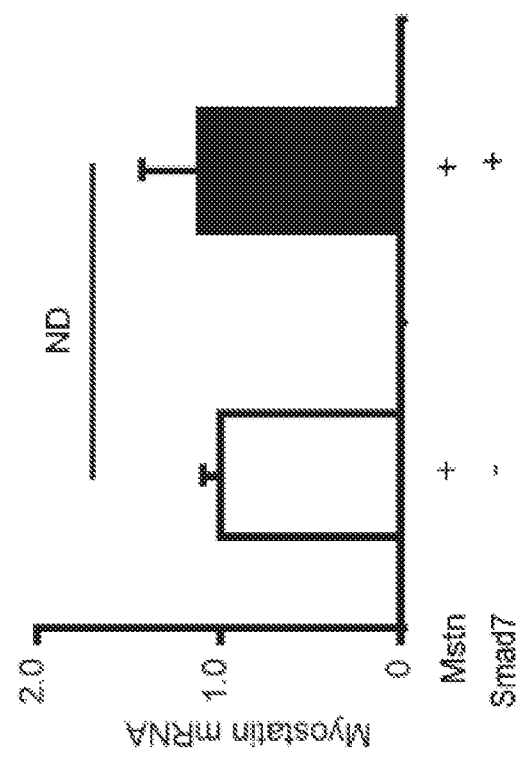

Although rAAV6:Smad7 induced similar absolute changes in muscle mass, increased fiber cross-sectional area and attenuated Smad3 phosphorylation, the relative changes in muscle mass were less pronounced in mstn-/- mice (FIG. 4A-4D). This is similar to the inherent limitations in musculature previously demonstrated by combining approaches to attenuate ActRIIB activity (Lee, *PLoS ONE* 2, e789, 2007) and when comparing the relative hypermuscularity of mstn-/- mice and cattle (Tellgren et al., *Mol Phylogenet Evol* 33, 782-790, 2004) as positive selection in bovids has resulted in modern species being "partially null". Nevertheless, the hypertrophic action of rAAV6:Smad7 in mstn-/- mice supports previous studies (Lee, *PLoS ONE* 2, e789, 2007; Lee et al., *Mol Endocrinol* 24, 1998-2008, 2010) demonstrating redundant actions of ActRIIB ligands (activin & GDF-11) and is supported by our recent study suggesting that Activin A and myostatin are similarly capable of stimulating muscle atrophy (Chen et al., *FASEB J.*, 28(4):1711-1723, 2014). In fact, transducing mice with rAAV6:activin or rAAV6:myostatin simultaneously induced muscle atrophy and increased Smad3 phosphorylation. These effects were completely prevented by co-administration of rAAV6:Smad7, which had no effect on either myostatin or activin A expression (FIG. 4E-4G; FIG. 5A-5C). Smad7 can therefore inhibit the redundant actions of multiple ActRIIB ligands in muscle.

Example 4: Increasing Smad7 Prevents Muscle Wasting Associated with Cancer Cachexia In this example, as ActRIIB signaling is hypothesized to contribute to the development and progression of cancer cachexia (Benny Klimek et al., *Biochem Biophys Res Commun* 391, 1548-1554, 2010; Zhou et al., *Cell* 142, 531-543, 2010; Zimmers et al., *Science* 296, 1486-1488, 2002; Coerver et al., *Mol Endocrinol* 10, 534-543, 1996; Lokireddy et al., *Biochem J* 446, 23-36, 2012), we examined whether rAAV6:Smad7 could prevent muscle wasting in mice bearing cachexia-inducing C-26 colon carcinoma-derived tumors.

Figure 6A:
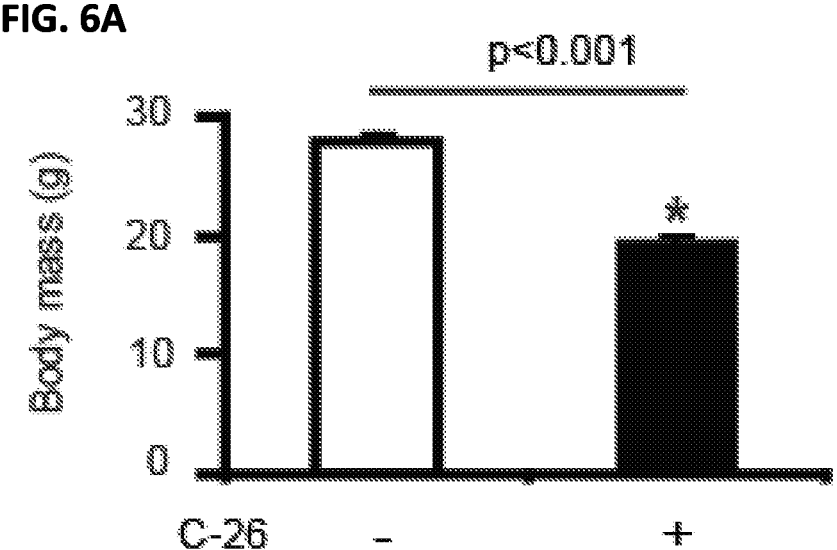
FIGS. 6A-6I show, according to particular aspects, cancer cachexia induced by C-26 tumor implantation.
Figure 6B:
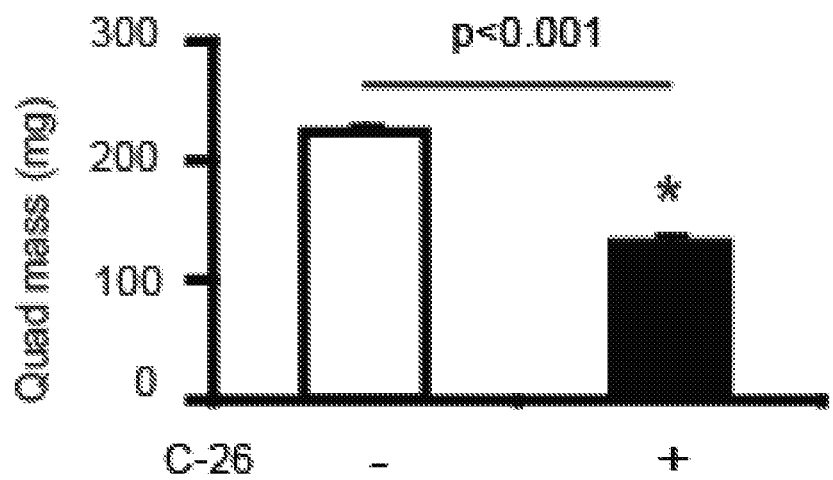
Figure 6C:
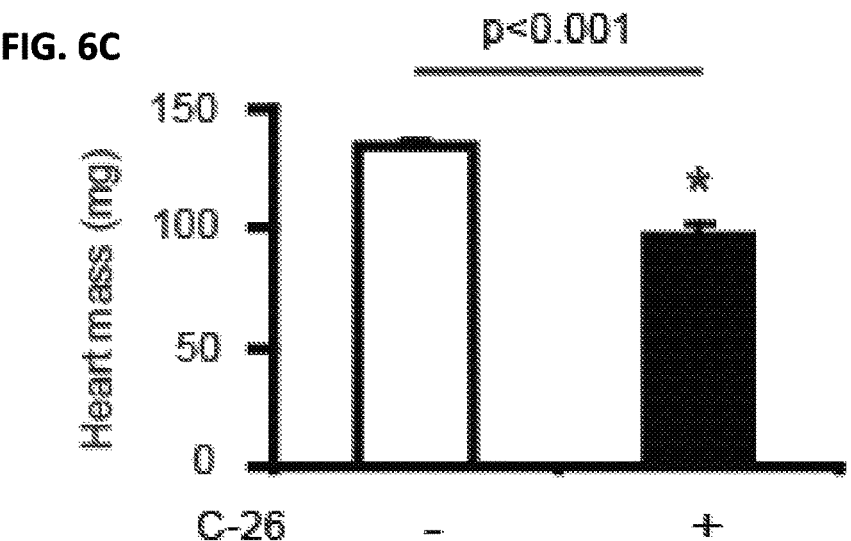
Figure 6D:
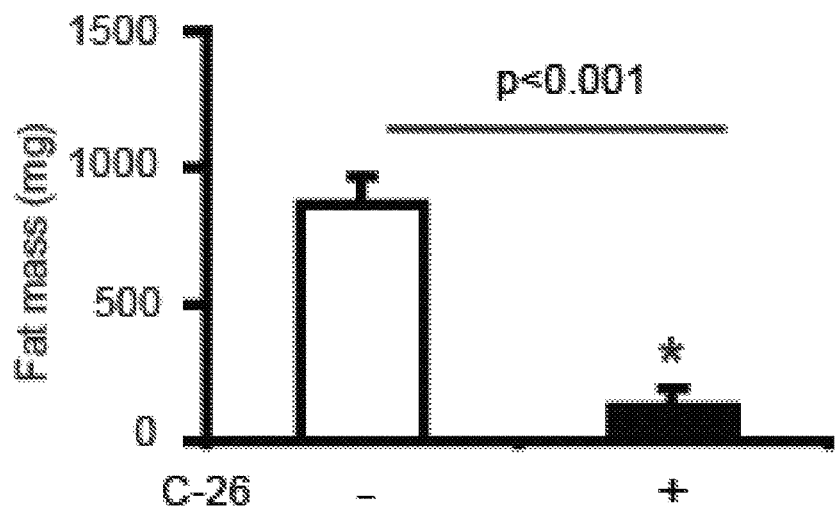
Figure 6E:
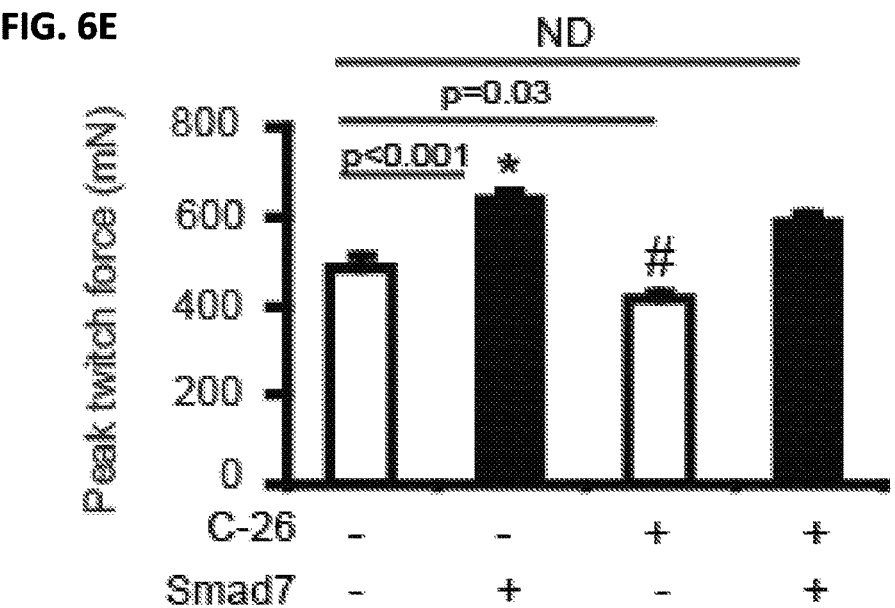
Figure 6F:
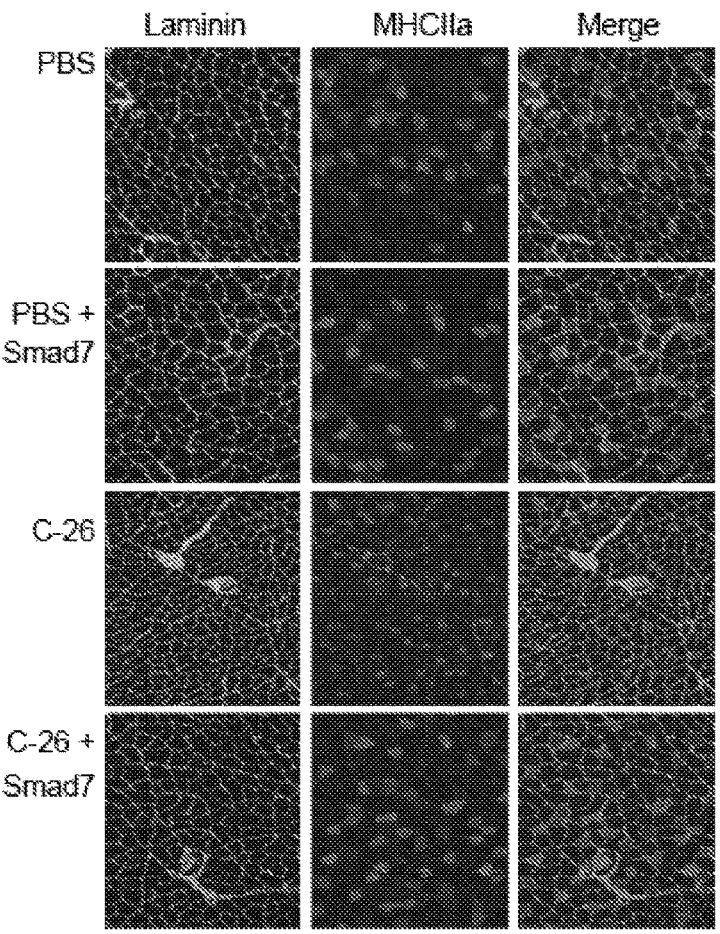
Figure 6G:
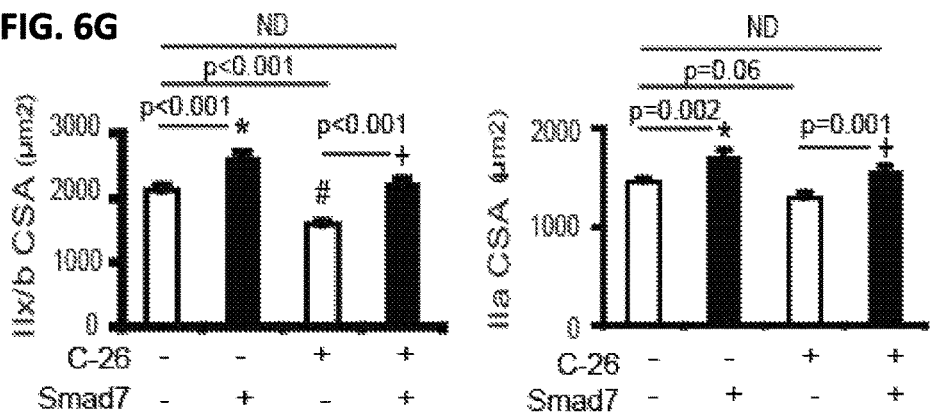
Figure 6H:
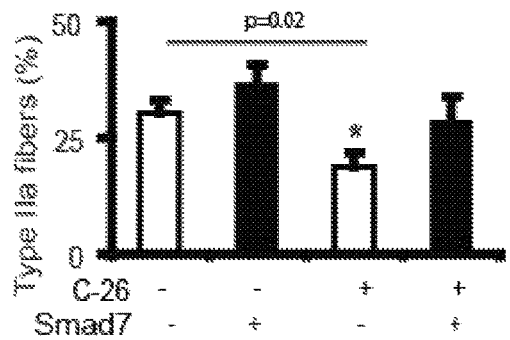
Figure 6I:
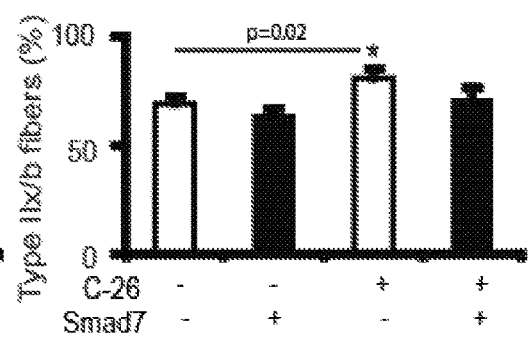
Figure 7A:
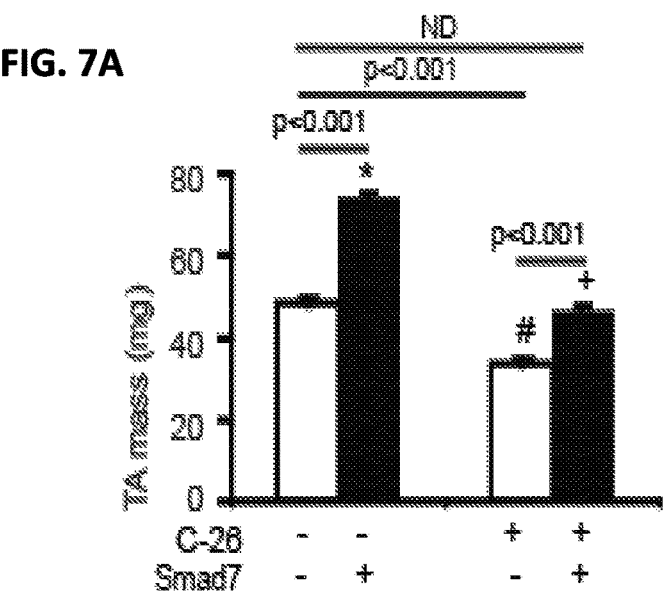
FIGS. 7A-7K show, according to particular aspects, increasing Smad7 expression prevents cancer cachexia.
Figure 7B:
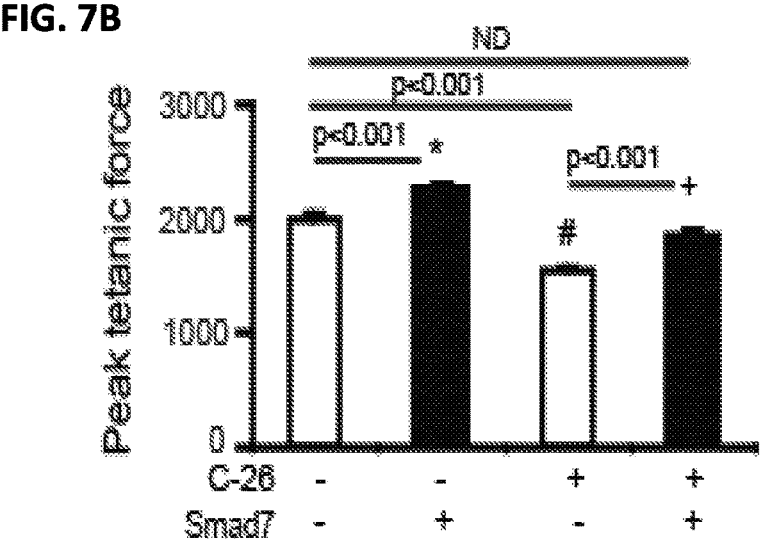
Figure 7C:
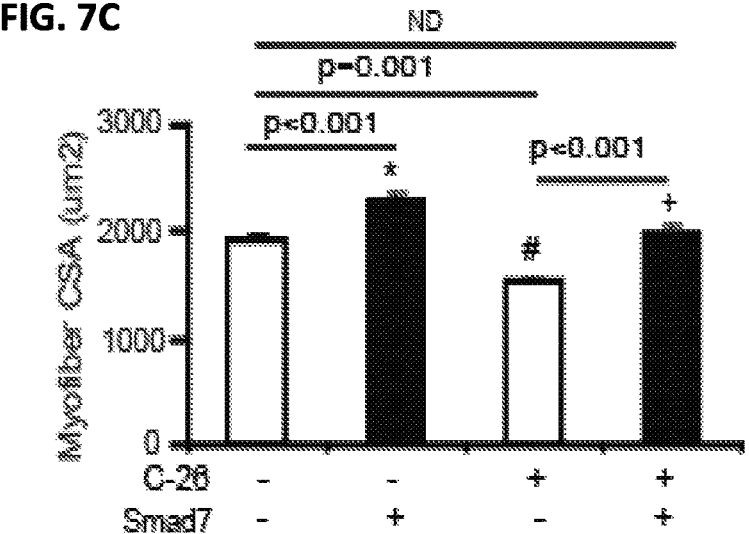
Figure 7D:
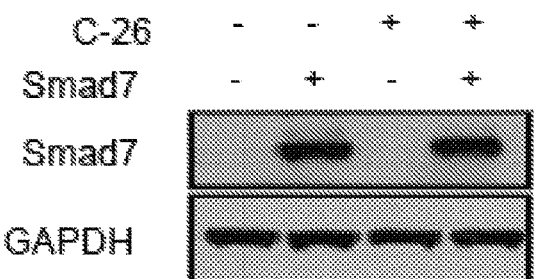
Figure 7E:
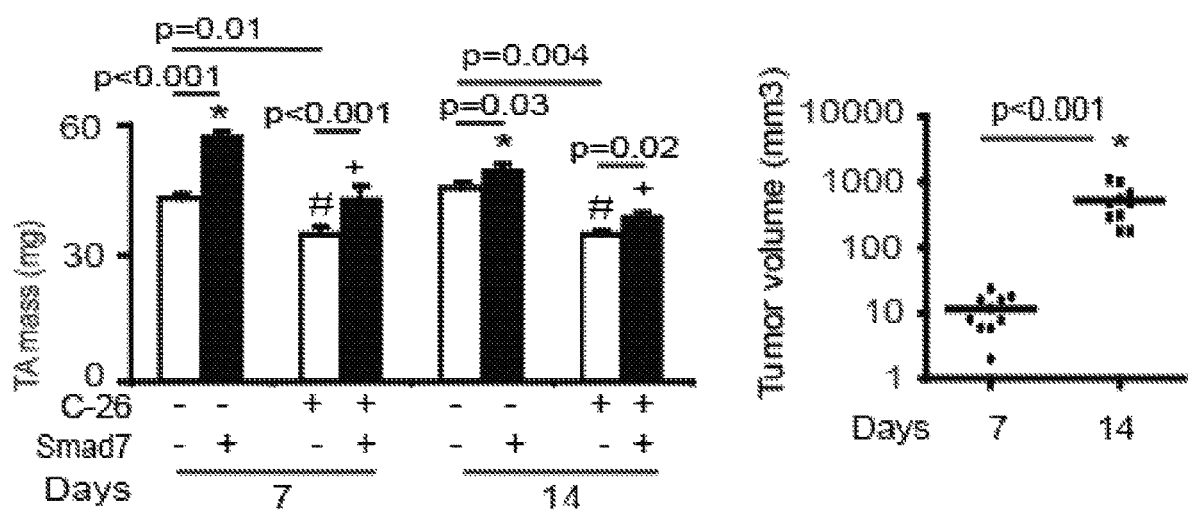
Figure 7F:
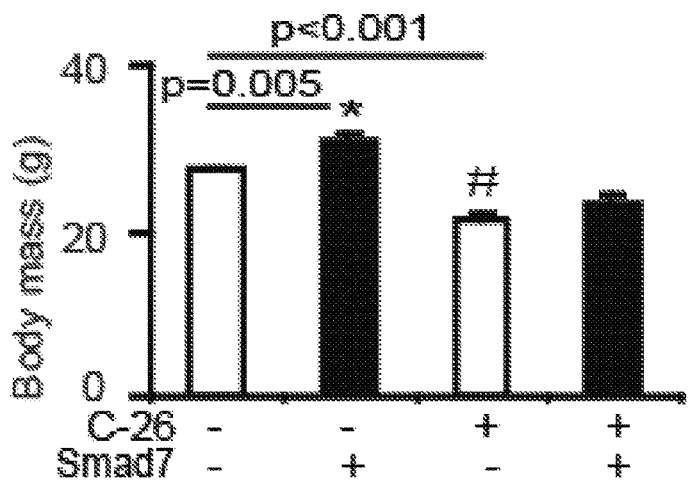
Figure 7G:
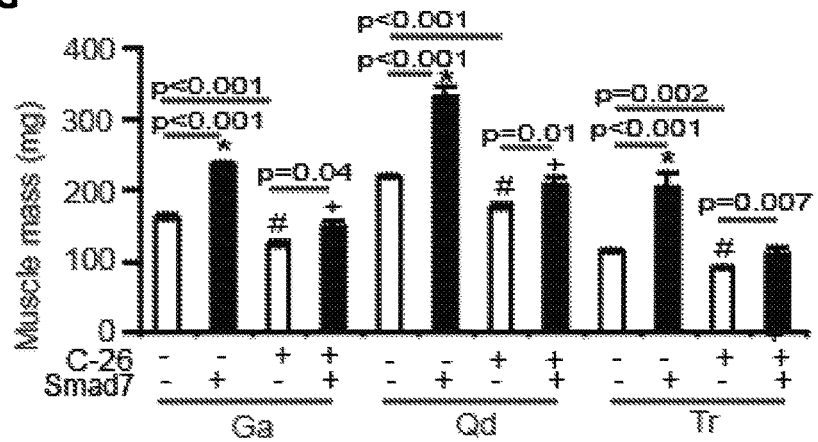
Figure 7H:
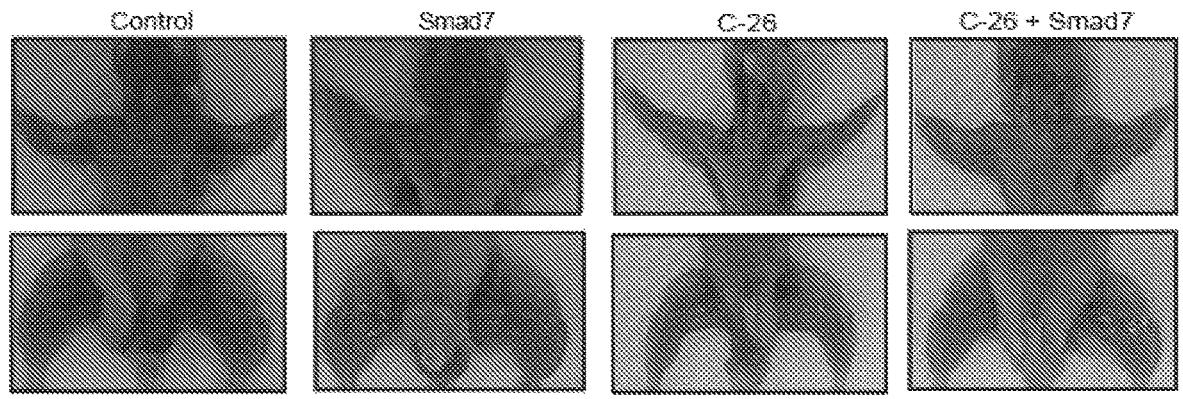
Figure 7I:
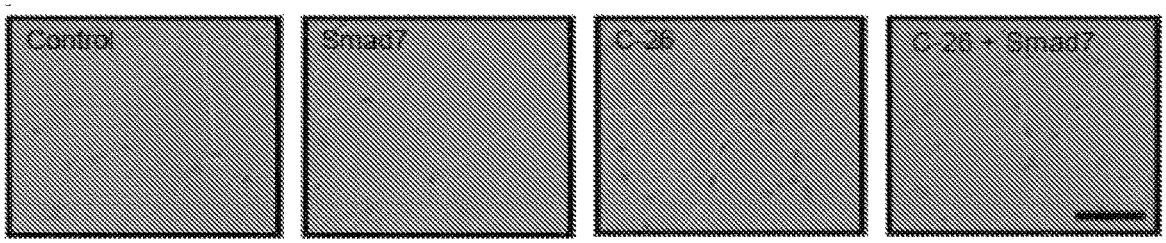

Body mass, skeletal muscle mass, heart and fat mass were all reduced in tumor-bearing mice (FIG. 5A-5D). In contrast, injecting rAAV6:Smad7 into the TA muscles of tumor-bearing mice completely prevented loss of muscle mass (FIG. 7A), peak isometric force (FIG. 7B, FIG. 6E) and muscle fiber cross sectional area (CSA, FIG. 7C). Cancer cachexia also decreased type IIa fiber distribution and increased that of type IIx/IIb, although rAAV6:Smad7 restored these proportions (FIG. 6F-6G). Muscle fiber number did not change with cachexia or rAAV6:Smad7 treatment (FIG. 6G-6I), indicating the tumor-mediated loss of muscle mass was due to atrophy, not apoptosis. As administering therapies for cachexia before muscle wasting develops may not always be possible, we examined whether injecting rAAV6:Smad7 at 7 or 14 days after tumor establishment was also protective. Examination of animals receiving a delayed administration of rAAV6:Smad7 revealed treatment still significantly ameliorated muscle atrophy (FIG. 7E).

Figure 7J:
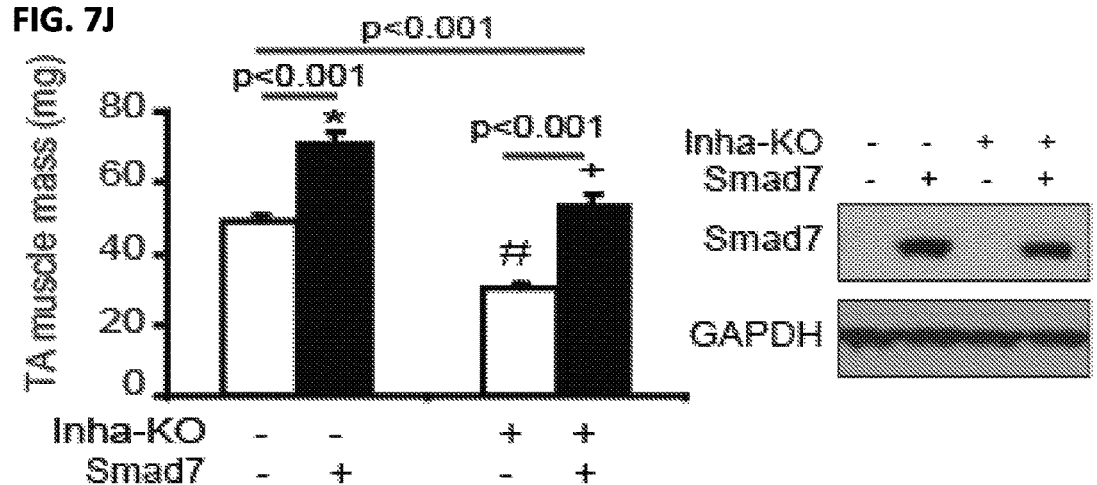
Figure 7K:
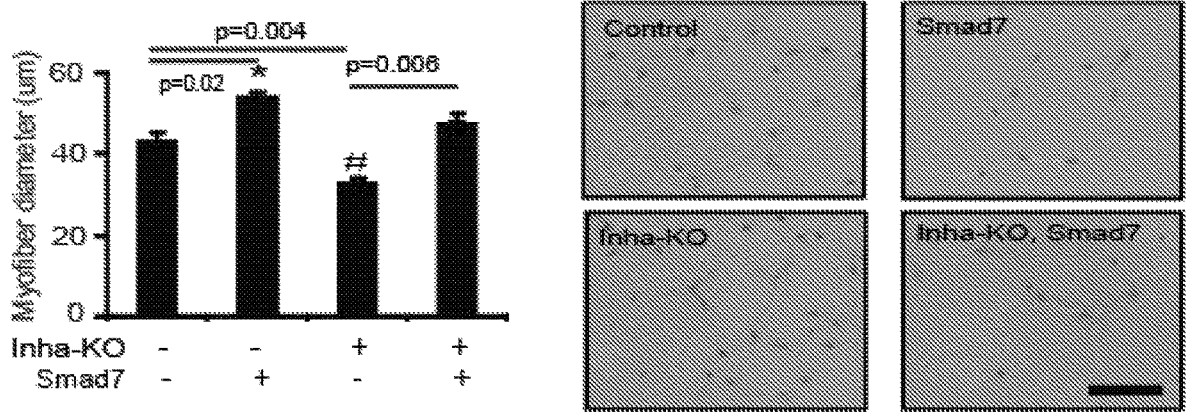
Figure 8B:
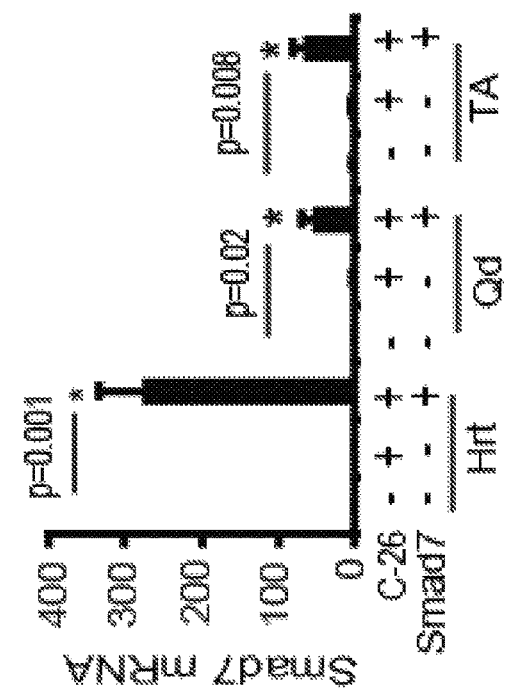
Figure 8A:
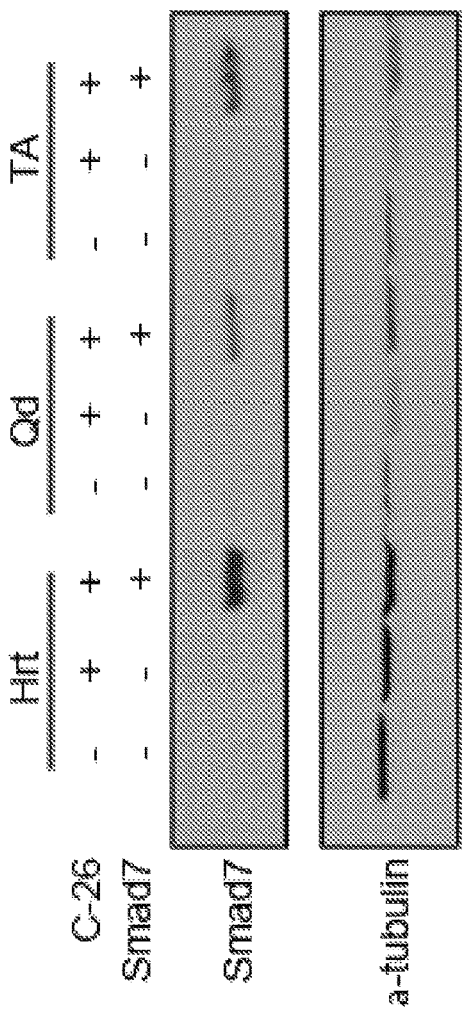
Figure 8C:
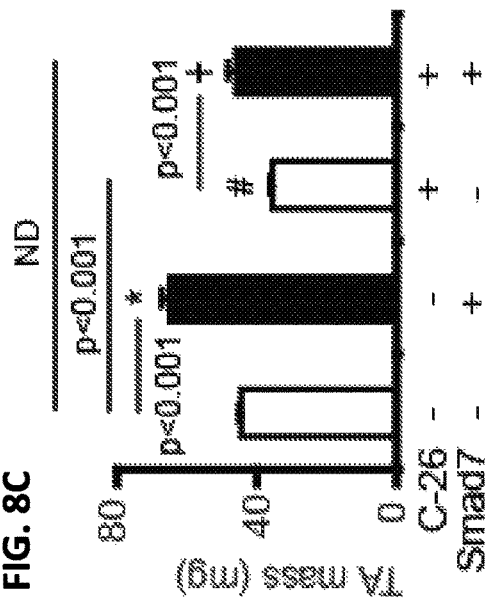
Figure 8H:
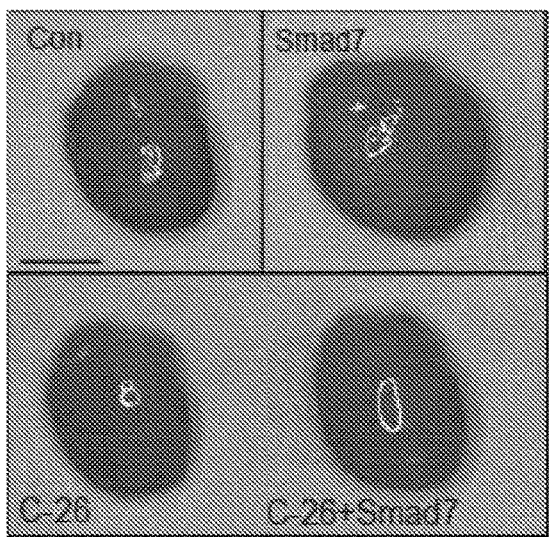
Figure 8I:
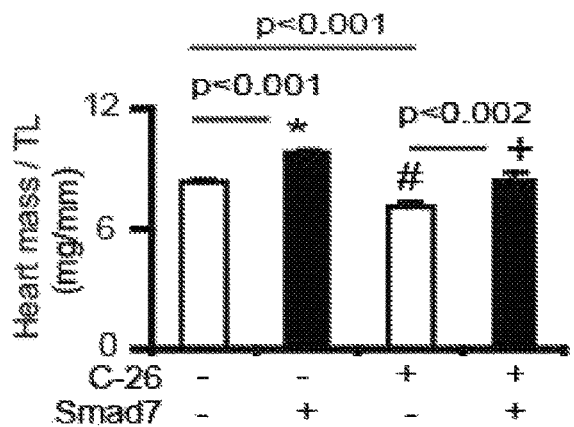
Figure 8J:
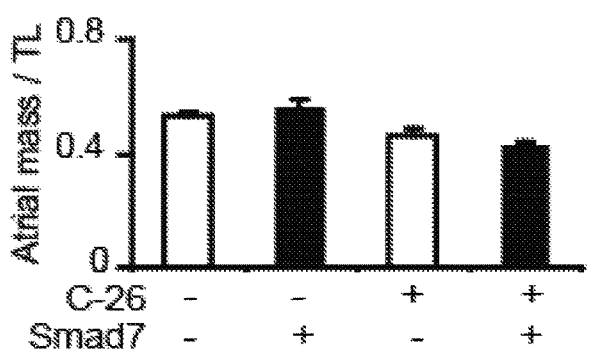
Figure 8K:
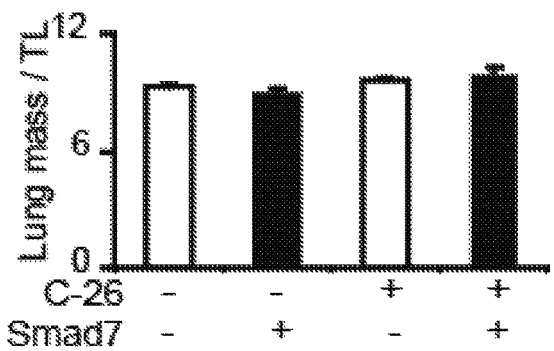
Figure 9B:
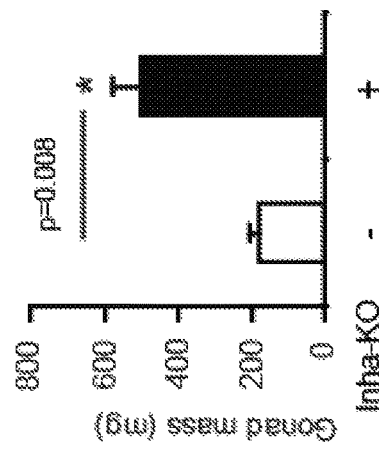
FIGS. 9A-9C show, according to particular aspects, inhibin-null mice exhibit progressive loss of lean and fat mass.
Figure 9C:
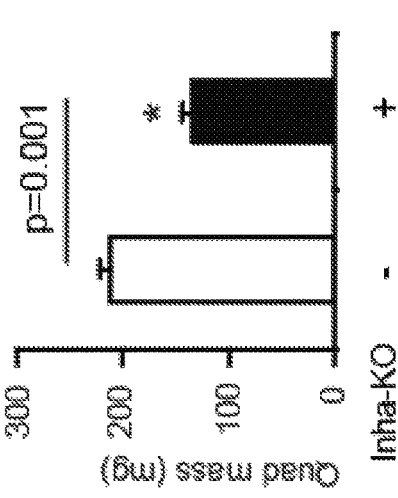
Figure 9A:
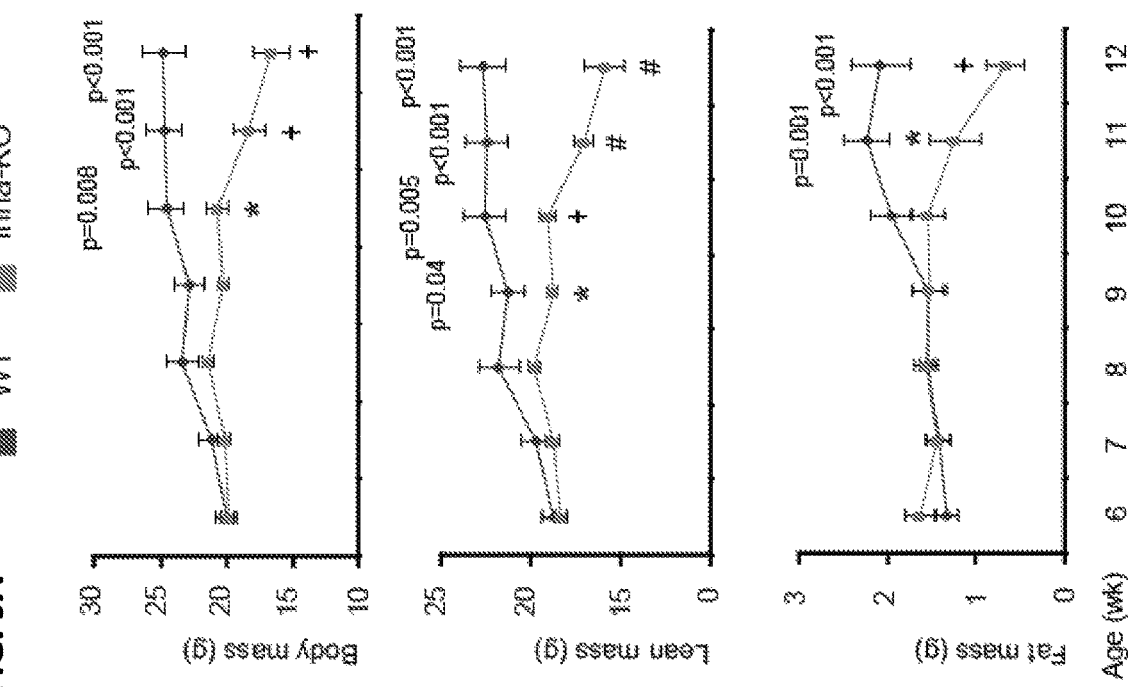

In an additional example, as cancer cachexia causes wasting of muscles throughout the body, we tested whether rAAV6:Smad7 could prevent muscle atrophy at a systemic level. Intravenous injection of rAAV6:Smad7 robustly increased Smad7 expression throughout the striated musculature of tumor bearing mice (FIG. 8A-8B). Treatment did not completely prevent reductions in body mass, but preserved the mass of skeletal muscles throughout the body (FIG. 7F-7I, FIG. 8C-8D), despite continued tumor development (FIG. 8E). We attribute the discrepancy between prevention of muscle atrophy and incomplete conservation of body mass to cachectic effects on other tissues (Fearon et al., *Cell Metabolism* 16, 153-166, 2012), primarily fat (FIG. 8F-8G). As cancer cachexia also affects the heart, it was encouraging to note that systemic rAAV6:Smad7 administration also prevented cardiac atrophy in tumor bearing mice (FIG. 8H-8I), and did not elicit increases in atrial mass or gross lung weight typically associated with heart failure (FIG. 8J-8K) (Bernardo et al., *Proc Natl Acad Sci USA* 109, 17615-17620, 2012). To confirm that the therapeutic effects of rAAV6:Smad7 in the setting of cachexia were not unique to the model employed, we tested the efficacy of our rAAV6:Smad7 intervention in inhibin-α knock-out mice, which exhibit profound cachexia subsequent to the development of gonadal tumors (FIG. 9A-9C) (Zhou et al., *Cell* 142, 531-543, 2010; Coerver et al., *Mol Endocrinol* 10, 534-543, 1996; Matzuk et al., *Nature* 360, 313-319, 1992). Consistent with results obtained from mice bearing C-26 tumors, we found that administration of rAAV6:Smad7 to the muscles of inhibin-α null mice prevented muscle atrophy (FIG. 7J-7K), thus demonstrating that rAAV6:Smad7 can prevent cachexia independent of tumor origin.

Figure 10A:
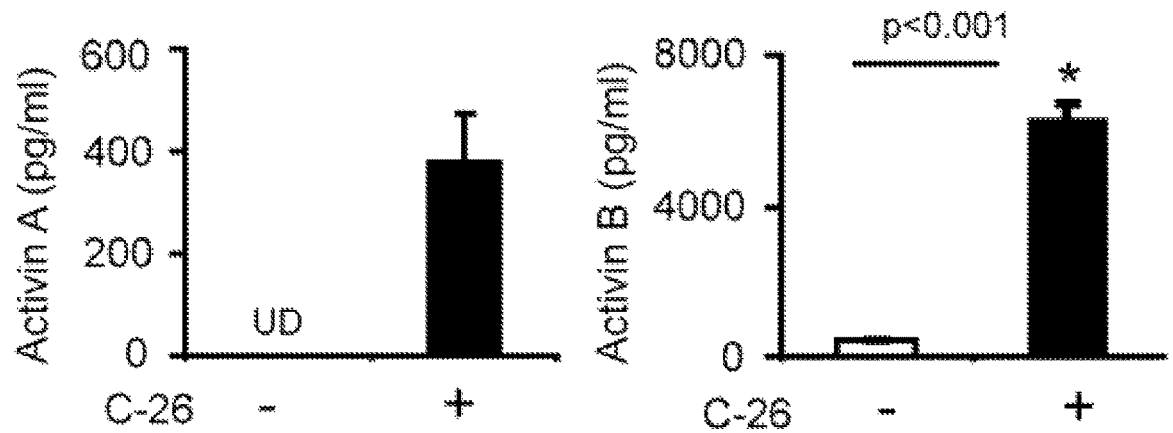
FIGS. 10A-10F show, according to particular aspects, Smad7 regulates the canonical TGFβ signaling pathway and E3 ligase expression to prevent muscle atrophy in cancer cachexia.
Figure 10B:
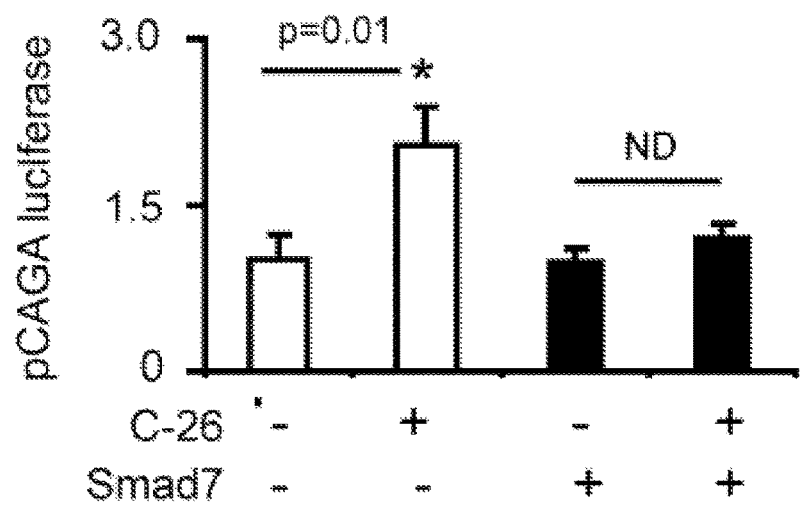
Figure 10C:
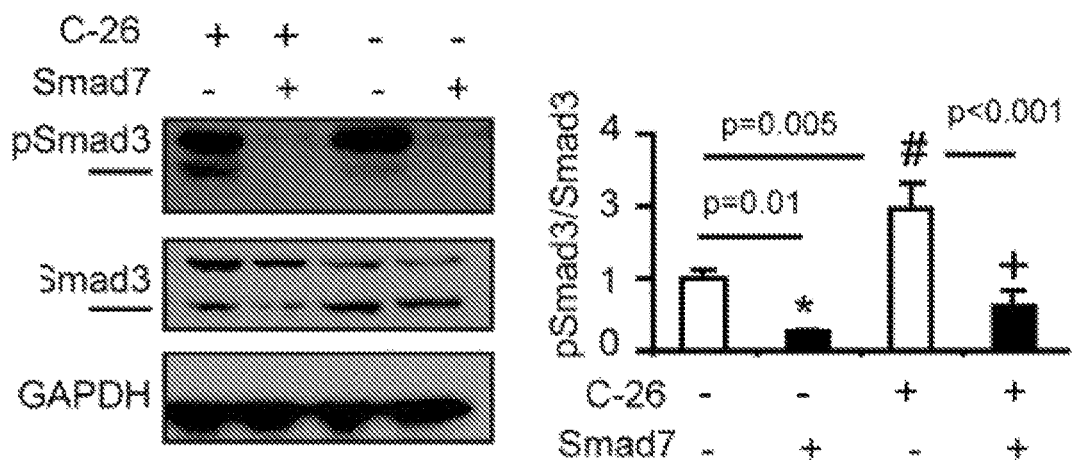
Figure 10C:
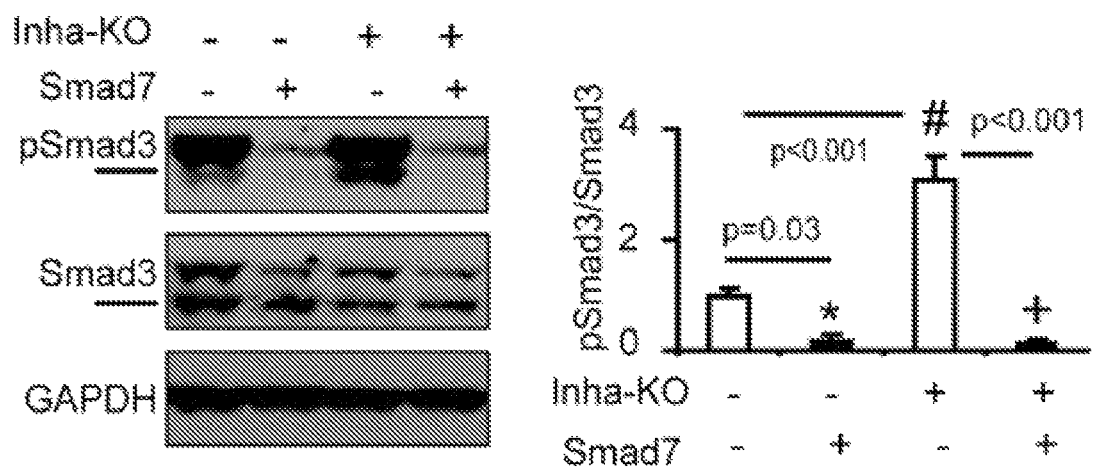
Figure 10D:
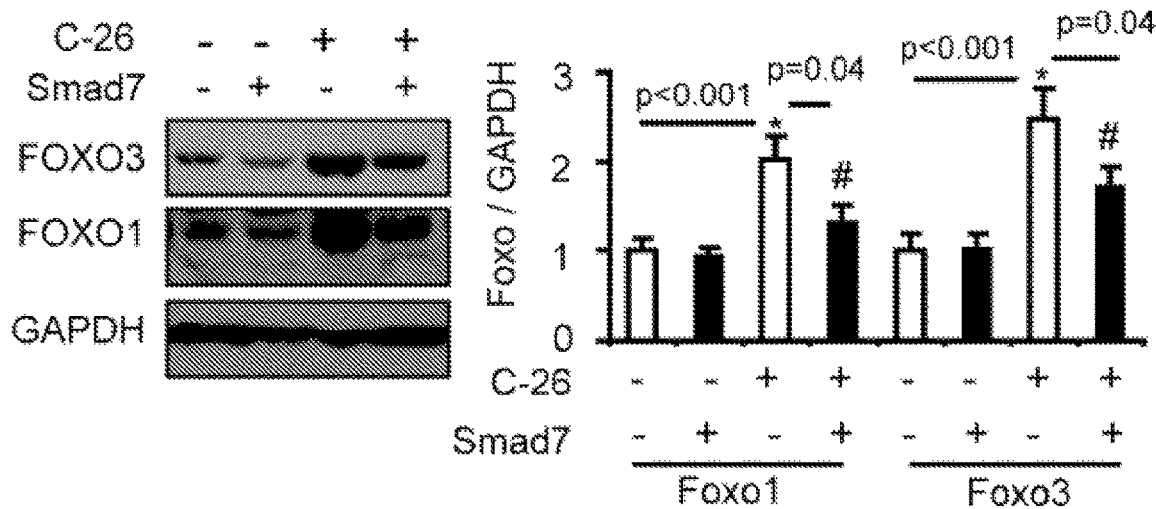
Figure 10E:
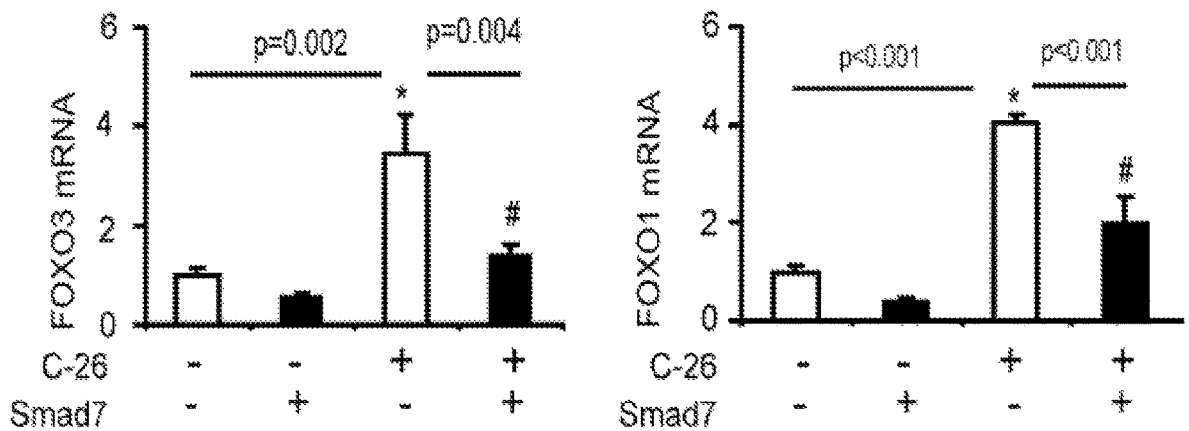
Figure 10F:
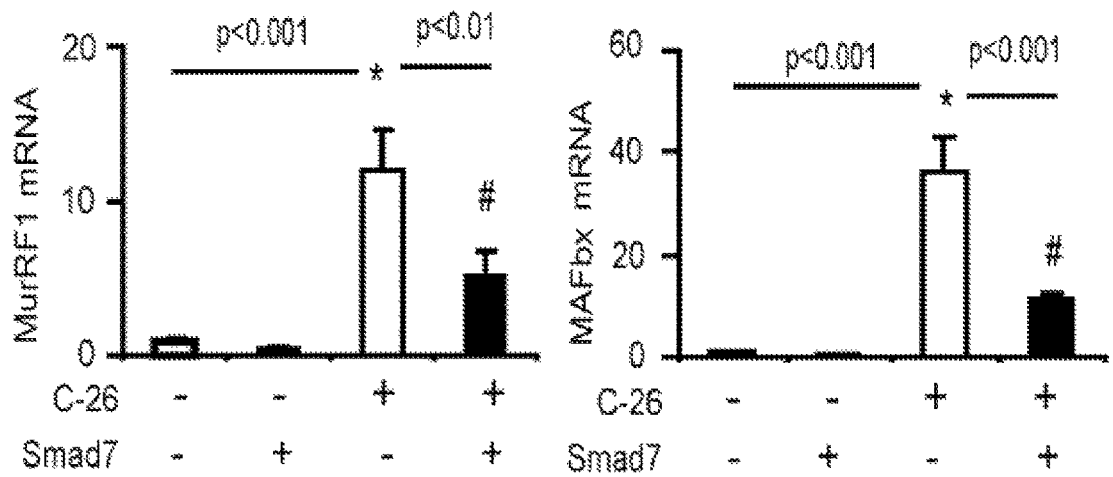
Figure 11D:
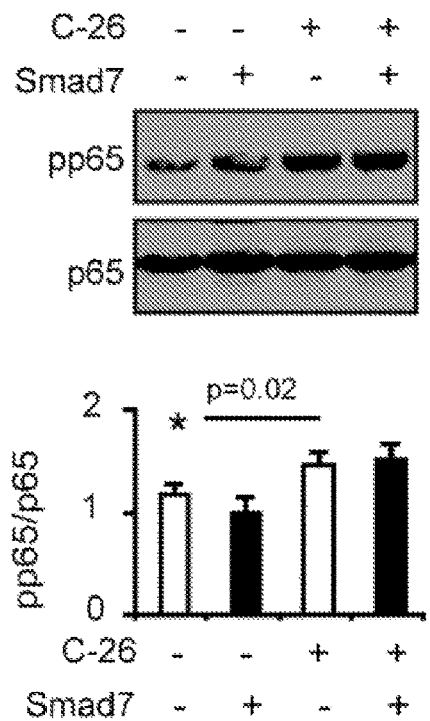
Figure 11E:
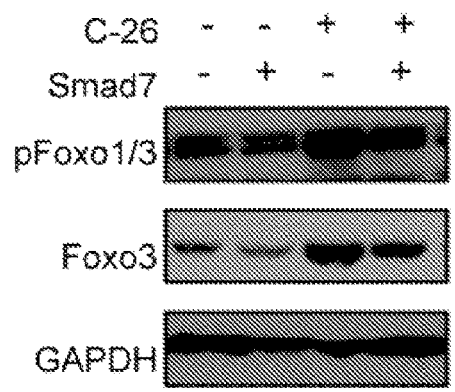
Figure 11E:
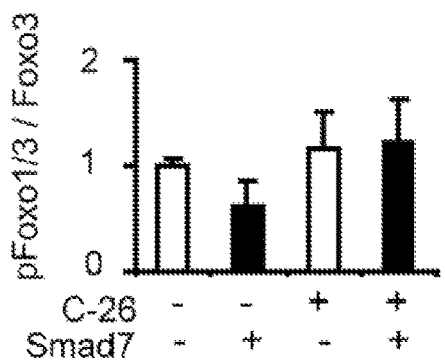

Example 5: Smad7 Prevents Muscle Wasting by Partially Inhibiting Ubiquitin Ligase Activation Downstream of ActRIIB Signaling In the cachectic models, Smad7 protected striated musculature from wasting despite circulating levels of activin A and B remaining elevated (serum from C-26 tumor-bearing mice remained capable of activating a Smad3-responsive luciferase reporter in C2C12 myogenic cells, FIG. 10A-10B, FIG. 11A). We attribute the protective effects of rAAV6:Smad7 in cachectic mice to the suppression of Smad3 transcription and phosphorylation in striated muscles (FIG. 10C-10D). However, as tumor and host-derived interleukin-6 (IL-6) is also implicated in the etiology of cachexia (Fearon et al., *Cell metabolism* 16, 153-166, 2012; Strassmann et al., *J Clin Invest* 89, 1681-1684, 1992; Fujita et al., *Int J Cancer* 68, 637-643, 1996; Bonetto et al., *Am J Physiol Endocrinol Metab* 303, E410-421, 2012), we examined whether the protective effects of Smad7 were associated with altered IL-6 signaling. Administration of rAAV6:Smad7 did not alter circulating levels of IL-6, or the phosphorylation of interleukin-responsive Stat3 in the muscles of tumor bearing mice (FIG. 11B-11C), nor did it affect p65 phosphorylation, a key regulator of NFκB signaling engaged by pro-cachectic cytokines (FIG. 11D). Interestingly, we found that although overexpression of Smad7 did not alter the ratio of phosphorylated to total Foxo1 or 3 (transcriptional regulators of MuRF1 and MAFbx (Sandri et al., *Cell* 117, 399-412, 2004; Stitt et al., *Mol Cell* 14, 395-403, 2004), FIG. 11E), treatment reduced abundance of Foxo1/3 in the muscles of tumor bearing mice resulting in reduced levels of the total phosphorylated forms (FIG. 10E-10F). As inhibiting Foxo1/3 transcription can ameliorate muscle wasting by repressing MuRF1 and MAFbx transcription (Reed et al., *FASEB J* 26, 987-1000, 2012), we examined the muscles of tumor bearing mice for effects of treatment upon the transcription of MuRF1 and MAFbx. We observed that administration of rAAV6:Smad7 suppressed MuRF1 and MAFbx expression in the muscles of tumor bearing mice, compared to mice receiving control vector (FIG. 10G).

Example 6: Treatment of Muscle Wasting Using Smad7

This example describes an exemplary method for the clinical use of rAAV vectors encoding Smad7 for the treatment of muscle wasting.

A subject diagnosed with muscle wasting (such as cancer cachexia) is selected for treatment. The subject is administered a therapeutically effective amount of a recombinant AAV expressing Smad7, such as a rAAV comprising SEQ ID NO: 5 or an equivalent thereof capable of expressing Smad7, as disclosed herein. In embodiments, the Smad7 is selected from to be from the same species as the subject. The recombinant AAV can be administered intravenously. An appropriate therapeutic dose can be selected by a medical practitioner. In some cases, the therapeutically effective dose is in the range of $1 \times 10^{10}$ to $1 \times 10^{14}$ viral particles (vp)/kg, such as about $1 \times 10^{11}$ or $1 \times 10^{12}$ vp/kg. In most instances, the composition is administered a single dose. In the absence of immunomodulation, the patient may tolerate only a single infusion of rAAV. If the subject has had pre-exposure immunomodulation, two or more doses may be administered. The health of the subject can be monitored over time to determine the effectiveness of the treatment.

Example 7: Enhancement of Muscle Mass and/or Strength Using Smad7

This example describes an exemplary method for the cosmetic use of rAAV vectors encoding Smad7 to increase or enhance muscle mass and/or strength. Having demonstrated herein that rAAV6:Smad7 increases muscle mass and strength in healthy mice, the methods and compositions described herein can be used in elective/cosmetic procedures in healthy subjects desiring increased muscle mass, strength, or both.

A subject desiring increased muscle mass and/or strength is selected for treatment. The subject is administered a therapeutically effective amount of a recombinant AAV expressing Smad7, such as a rAAV comprising SEQ ID NO: 5 or an equivalent thereof capable of expressing Smad7, as disclosed herein. In embodiments, the Smad7 is selected from to be from the same species as the subject. The recombinant AAV can be administered intravenously. An appropriate therapeutic dose can be selected by a medical practitioner. In some cases, the therapeutically effective dose is in the range of $1 \times 10^{10}$ to $1 \times 10^{14}$ viral particles (vp)/kg, such as about $1 \times 10^{11}$ or $1 \times 10^{12}$ vp/kg. In most instances, the composition is administered a single dose. In the absence of immunomodulation, the patient may tolerate only a single infusion of rAAV. If the subject has had pre-exposure immunomodulation, two or more doses may be administered. The health of the subject can be monitored over time to determine the effectiveness of the treatment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A composition comprising a Smad7 gene or cDNA in a recombinant adeno-assisted virus (rAAV) construct, wherein the rAAV construct is a serotype 6 (rAAV6), serotype 8 (rAAV8), or serotype 9 (rAAV9) construct, and the rAAV construct provides expression of the Smad7 gene or cDNA in muscle cells.

2. The composition of claim 1, wherein the rAAV construct is a rAAV6 construct.

3. The composition of claim 1, wherein the Smad7 gene or cDNA is of human, mouse, equine, bovine, ovine, canine, or porcine origin.

4. The composition of claim 1, wherein the Smad7 gene or cDNA expressed is a constitutively active mutant.

5. The composition of claim 1, wherein the rAAV construct comprises a tissue-specific promoter or enhancer that directs expression of the Smad7 gene or cDNA in muscle cells.

6. The composition of claim 5, wherein the rAAV construct provides expression of the Smad7 gene or cDNA in cardiac muscle cells, skeletal muscle cells, or both.

7. The composition of claim 1, wherein the rAAV construct comprises a tissue-specific silencer that limits expression of the Smad7 gene or cDNA to muscle cells or to heart cells.

8. A composition comprising a Smad7 gene or cDNA in a recombinant adeno-assisted virus (rAAV) construct, wherein the Smad7 gene or cDNA is of human origin, and wherein the rAAV construct is a serotype 6 (rAAV6), serotype 8 (rAAV8), or serotype 9 (rAAV9) construct, and the rAAV construct provides expression of the Smad7 gene or cDNA in muscle cells.

* * * * *

SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1
ggagtgtgat ggcaaggtca aca                    23

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
gtgggcacac agcatgactt a                      21

<210> SEQ ID NO 3

```
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
cccagaggtt cagcaggccc t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
tcatgagcac ccacagcggt c                                              21

<210> SEQ ID NO 5
<211> LENGTH: 6018
<212> TYPE: DNA
<213> ORGANISM: Artificial Sequence
<220> FEATURE:
<223> OTHER INFORMATION: Smad7 AAV vector, pAAV-MCS_smad7stp 081809.cep;
      contains murine Smad7 encoding sequence

<400> SEQUENCE: 5
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtggagc tagttattaa tagtaatcaa    180
ttacggggtc attagttcat agcccatata tggagttccg cgttacataa cttacggtaa    240
atggcccgcc tggctgaccg cccaacgacc cccgcccatt gacgtcaata atgacgtatg    300
ttcccatagt aacgtcaata gggactttcc attgacgtca atgggtggag tatttacggt    360
aaactgccca cttggcagta catcaagtgt atcatatgcc aagtacgccc cctattgacg    420
tcaatgacgg taaatggccc gcctggcatt atgcccagta catgacctta tgggactttc    480
ctacttggca gtacatctac gtattagtca tcgctattac catggtgatg cggttttggc    540
agtacatcaa tgggcgtgga tagcggtttg actcacgggg atttccaagt ctccacccca    600
ttgacgtcaa tgggagtttg ttttgcacca aaatcaacgg gactttccaa aatgtcgtaa    660
caactccgcc ccattgacgc aaatgggcgg taggcgtgta cggtgggagg tctatataag    720
cagagctcgt ttagtgaacc gtcagatcgc ctggagacgc catccacgct gttttgacct    780
ccatagaaga caccgggacc gatccagcct ccgcggattc gaatcccggc cgggaacggt    840
gcattggaac gcggattccc cgtgccaaga gtgacgtaag taccgcctat agagtctata    900
ggcccacaaa aaatgctttc ttcttttaat atactttttt gtttatctta tttctaatac    960
tttccctaat ctctttcttt cagggcaata atgatacaat gtatcatgcc tctttgcacc   1020
attctaaaga ataacagtga taatttctgg gttaaggcaa tagcaatatt tctgcatata   1080
aatatttctg catataaatt gtaactgatg taagaggttt catattgcta atagcagcta   1140
caatccagct accattctgc ttttatttta tggttgggat aaggctggat tattctgagt   1200
ccaagctagg ccttttgct aatcatgttc atacctctta tcttcctccc acagctcctg   1260
ggcaacgtgc tggtctgtgt gctggcccat cactttggca aagaattggg attcgaacat   1320
cgattgaatt cgcccttgtc atgttcgctc cttagccggc aaacgacttt tctcctcgcc   1380
```

-continued

```
tcctcgcccc gcatgttcag gaccaaacga tctgcgctcg tccggcgtct ctggaggagc    1440
cgtgcgcccg gcggcgagga cgaggaggag ggcgtggggg gtggcggcgg aggaggcgag    1500
ctgcggggag aagggcgac ggacggccgg gcttatgggg ctggtggcgg cggtgcgggc     1560
agggctggct gctgcctggg caaggcagtc cgaggtgcca aaggtcacca ccatccccat    1620
cccccaacct cgggtgccgg ggcggccggg ggcgccgagg cggatctgaa ggcgctcacg    1680
cactcggtgc tcaagaaact caaggagcgg cagctgagc tgctgcttca ggccgtggag     1740
tcccgcggcg gtacgcgcac cgcgtgcctc ctgctgcccg gccgcctgga ctgcaggctg    1800
ggccggggg cgcccgccag cgcgcagccc gcgcagccgc cctcgtccta ctcgctcccc     1860
ctcctgctgt gcaaagtgtt caggtggccg gatctcaggc attcctcgga agtcaagagg    1920
ctgtgttgct gtgaatctta cgggaagatc aaccccgagc tggtgtgctg caaccccat    1980
caccttagtc gactctgtga actagagtct cccctcctc cttactccag atacccaatg     2040
gattttctca aaccaactgc aggctgtcca gatgctgtac cttcctccgc ggaaaccggg    2100
ggaacgaatt atctggcccc tggggggctt tcagattccc aacttcttct ggagcctggg    2160
gatcggtcac actggtgcgt ggtggcatac tgggaggaga agactcgcgt ggggaggctc    2220
tactgtgtcc aagagccctc cctggatatc ttctatgatc tacctcaggg gaatggcttt    2280
tgcctcggac agctcaattc ggacaacaag agtcagctgg tacagaaagt gcggagcaag    2340
atcggctgtg gcatccagct gacgcgggaa gtggatggcg tgtgggttta caaccgcagc    2400
agttacccca tcttcatcaa gtccgccaca ctggacaacc cggactccag gacgctgttg    2460
gtgcacaaag tgttccctgg tttctccatc aaggcttttg actatgagaa agcctacagc    2520
ctgcagcggc ccaatgacca cgagttcatg cagcaaccat ggacggggttt caccgtgcag    2580
atcagctttg tgaagggctg gggccagtgc tacacccgcc agttcatcag cagctgcccg    2640
tgctggctgg aggtcatctt caacagccgg tagtcggtcg tgtggtgaag ggcgaattcc    2700
ccggggatcc tctagagtcg acctgcagaa gcttgcctcg agcagcgctg ctcgagagat    2760
ctacgggtgg catccctgtg accctccc agtgcctctc ctggccctgg aagttgccac    2820
tccagtgccc accagcctg tcctaataaa attaagttgc atcatttgt ctgactaggt     2880
gtccttctat aatattatgg ggtggagggg ggtggtatgg agcaaggggc aagttgggaa    2940
gacaacctgt agggcctgcg gggtctattg ggaaccaagc tggagtgcag tggcacaatc    3000
ttggctcact gcaatctccg cctcctgggt tcaagcgatt ctcctgcctc agcctcccga    3060
gttgttggga ttccaggcat gcatgaccag gctcagctaa ttttttgtttt tttggtagag    3120
acggggtttc accatattgg ccaggctggt ctccaactcc taatctcagg tgatctaccc    3180
accttggcct cccaaattgc tgggattaca ggcgtgaacc actgctccct tcctgtcct    3240
tctgattttg taggtaacca cgtgcggacc gagcggccgc aggaaccct agtgatggag     3300
ttggccactc cctctctgcg cgctcgctcg ctcactgagg ccgggcgacc aaaggtcgcc    3360
cgacgcccgg gctttgcccg gcggcctca gtgagcgagc gagcgcgcag ctgcctgcag    3420
gggcgcctga tgcggtattt tctccttacg catctgtgcg gtatttcaca ccgcatacgt    3480
caaagcaacc atagtacgcg ccctgtagcg gcgcattaag cgcggcgggt gtggtggtta    3540
cgcgcagcgt gaccgctaca cttgccagcg ccctagcgcc cgctcctttc gctttcttcc    3600
cttcctttct cgccacgttc gccggctttc cccgtcaagc tctaaatcgg ggctccctt     3660
tagggttccg atttagtgct ttacggcacc tcgaccccaa aaaacttgat ttgggtgatg    3720
gttcacgtag tgggccatcg ccctgataga cggtttttcg ccctttgacg ttggagtcca    3780
```

```
cgttctttaa tagtggactc ttgttccaaa ctggaacaac actcaaccct atctcgggct   3840
attcttttga tttataaggg attttgccga tttcggccta ttggttaaaa aatgagctga   3900
tttaacaaaa atttaacgcg aattttaaca aaatattaac gtttacaatt ttatggtgca   3960
ctctcagtac aatctgctct gatgccgcat agttaagcca gccccgacac ccgccaacac   4020
ccgctgacgc gccctgacgg gcttgtctgc tcccggcatc cgcttacaga caagctgtga   4080
ccgtctccgg gagctgcatg tgtcagaggt tttcaccgtc atcaccgaaa cgcgcgagac   4140
gaaagggcct cgtgatacgc ctatttttat aggttaatgt catgataata atggtttctt   4200
agacgtcagg tggcactttt cggggaaatg tgcgcggaac ccctatttgt ttatttttct   4260
aaatacattc aaatatgtat ccgctcatga caataaacc ctgataaatg cttcaataat   4320
attgaaaaag gaagagtatg agtattcaac atttccgtgt cgcccttatt ccctttttg   4380
cggcattttg ccttcctgtt tttgctcacc cagaaacgct ggtgaaagta aaagatgctg   4440
aagatcagtt gggtgcacga gtgggttaca tcgaactgga tctcaacagc ggtaagatcc   4500
ttgagagttt tcgccccgaa gaacgttttc caatgatgag cacttttaaa gttctgctat   4560
gtggcgcggt attatcccgt attgacgccg ggcaagagca actcggtcgc cgcatacact   4620
attctcagaa tgacttggtt gagtactcac cagtcacaga aaagcatctt acggatggca   4680
tgacagtaag agaattatgc agtgctgcca taaccatgag tgataacact gcggccaact   4740
tacttctgac aacgatcgga ggaccgaagg agctaaccgc ttttttgcac aacatggggg   4800
atcatgtaac tcgccttgat cgttgggaac cggagctgaa tgaagccata ccaaacgacg   4860
agcgtgacac cacgatgcct gtagcaatgg caacaacgtt gcgcaaacta ttaactggcg   4920
aactacttac tctagcttcc cggcaacaat taatagactg gatggaggcg gataaagttg   4980
caggaccact tctgcgctcg gcccttccgg ctggctggtt tattgctgat aaatctggag   5040
ccggtgagcg tgggtctcgc ggtatcattg cagcactggg gccagatggt aagccctccc   5100
gtatcgtagt tatctacacg acggggagtc aggcaactat ggatgaacga atagacaga   5160
tcgctgagat aggtgcctca ctgattaagc attggtaact gtcagaccaa gtttactcat   5220
atatacttta gattgattta aaacttcatt tttaatttaa aaggatctag gtgaagatcc   5280
tttttgataa tctcatgacc aaaatccctt aacgtgagtt ttcgttccac tgagcgtcag   5340
accccgtaga aaagatcaaa ggatcttctt gagatccttt ttttctgcgc gtaatctgct   5400
gcttgcaaac aaaaaaacca ccgctaccag cggtggtttg tttgccggat caagagctac   5460
caactctttt tccgaaggta actggcttca gcagagcgca gataccaaat actgtccttc   5520
tagtgtagcc gtagttaggc caccacttca agaactctgt agcaccgcct acatacctcg   5580
ctctgctaat cctgttacca gtggctgctg ccagtggcga taagtcgtgt cttaccgggt   5640
tggactcaag acgatagtta ccggataagg cgcagcggtc gggctgaacg ggggggttcgt   5700
gcacacagcc cagcttggag cgaacgacct acaccgaact gagatacccta cagcgtgagc   5760
tatgagaaag cgccacgctt cccgaaggga gaaaggcgga caggtatccg gtaagcggca   5820
gggtcggaac aggagagcgc acgagggagc ttccaggggg aaacgcctgg tatctttata   5880
gtcctgtcgg gtttcgccac ctctgacttg agcgtcgatt tttgtgatgc tcgtcagggg   5940
ggcggagcct atgaaaaaac gccagcaacg cggccttttt acggttcctg ccttttgct   6000
ggccttttgc tcacatgt                                                6018
```